United States Patent
Iriki et al.

(10) Patent No.: US 10,342,475 B2
(45) Date of Patent: Jul. 9, 2019

(54) THRESHOLD ESTIMATION APPARATUS, THRESHOLD ESTIMATION METHOD, AND NON-TRANSITORY COMPUTER-READABLE INFORMATION RECORDING MEDIUM

(71) Applicant: RIKEN, Saitama (JP)

(72) Inventors: Atsushi Iriki, Saitama (JP); Junichi Ushiba, Saitama (JP); Mitsuaki Takemi, Saitama (JP)

(73) Assignee: RIKEN, Saitama (JP)

( * ) Notice: Subject to any disclaimer, the term of this patent is extended or adjusted under 35 U.S.C. 154(b) by 735 days.

(21) Appl. No.: 14/821,117

(22) Filed: Aug. 7, 2015

(65) Prior Publication Data
US 2016/0128620 A1 May 12, 2016

(30) Foreign Application Priority Data

Nov. 12, 2014 (JP) .................................. 2014-229524
Jul. 31, 2015 (JP) .................................. 2015-151520

(51) Int. Cl.
*A61B 5/00* (2006.01)
*A61B 5/0488* (2006.01)
(Continued)

(52) U.S. Cl.
CPC ........ *A61B 5/4064* (2013.01); *A61B 5/04001* (2013.01); *A61B 5/0488* (2013.01);
(Continued)

(58) Field of Classification Search
CPC . A61B 5/4064; A61B 5/04001; A61B 5/0484; A61B 5/0448; A61B 5/0478
See application file for complete search history.

(56) References Cited

U.S. PATENT DOCUMENTS 7,177,674 B2 * 2/2007 Echauz ................ A61B 5/0476
600/544
2003/0073917 A1 4/2003 Echauz et al.
(Continued)

FOREIGN PATENT DOCUMENTS

JP 2007-511328 A 5/2007
JP 2012-505707 A 3/2012
(Continued)

OTHER PUBLICATIONS

Mishory et al.; "The Maximum-likelihood Strategy for Determining Transcranial Magnetic Stimulation Motor Threshold, Using Parameter Estimation by Sequential Testing Is Faster Than Conventional Methods With Similar Precision"; J ECT, vol. 20, No. 3, Sep. 2004, pp. 160-165.
(Continued)

*Primary Examiner* — Daniel L Cerioni
*Assistant Examiner* — Yasmeen S Warsi
(74) *Attorney, Agent, or Firm* — Ohlandt, Greeley, Ruggiero & Perle, L.L.P.

(57) ABSTRACT

In a threshold estimation apparatus, a setting unit sets an initial intensity value for each electrode. A selection unit randomly selects an electrode. A stimulation unit, via the selected electrode, stimulates a living subject at an intensity set for the electrode. A detection unit detects the presence or absence of a response evoked by the stimulation. An update unit reduces or increases the intensity associated with the selected electrode, based on the presence or absence of the response evoked by the stimulation. An estimation unit, if the thus updated intensity associated with each electrode satisfies a convergence condition, estimates a convergence value as a threshold associated with the electrode. The threshold estimation apparatus repeats these processes until thresholds associated with all electrodes are estimated. If the
(Continued)

same electrode was consecutively selected, the time interval between a stimulation and a subsequent stimulation is adjusted.

24 Claims, 13 Drawing Sheets

(51) Int. Cl.
    *A61B 5/04* (2006.01)
    *A61N 1/37* (2006.01)
    *A61N 1/36* (2006.01)
(52) U.S. Cl.
    CPC ........ *A61N 1/3605* (2013.01); *A61N 1/36017* (2013.01); *A61N 1/3712* (2013.01)

(56) References Cited

U.S. PATENT DOCUMENTS

2005/0182456 A1* 8/2005 Ziobro ................ A61B 5/0488
    607/48
2011/0313314 A1* 12/2011 Gefen ................ A61B 5/0051
    600/555

FOREIGN PATENT DOCUMENTS

JP    2012-529947 A    11/2012
JP    2014-515296 A    6/2014

OTHER PUBLICATIONS

Raffin et al.; "Transcranial Brain Stimulation to Promote Functional Recovery After Stroke"; Current Opinion Neurol, vol. 27, No. 1, Feb. 2014, pp. 54-59.
Castel-Lacanal et al.; "Induction of Cortical Plastic Changes in Wrist Muscles by Paired Associative Stimulation in the Recovery Phase of Stroke Patients", Neurorehabilitation and Neural Repair, 2009, pp. 366-372.
Awiszus, Friedemann; "TMS and Threshold Hunting", Transcranial Magnetic Stimulation and Transcranial Direct Current Stimulation, vol. 56, 2003, pp. 13-23.
Japanese Notification of Reasons for Rejection dated Mar. 12, 2019 from corresponding Japanese Patent Application No. 2015/151520, 7 pages.
Mills et al.; "Corticomotor Threshold to Magnetic Stimulation: Normal Values and Repeatability"; Muscle & Nerve, May 1997, pp. 570-576.

* cited by examiner

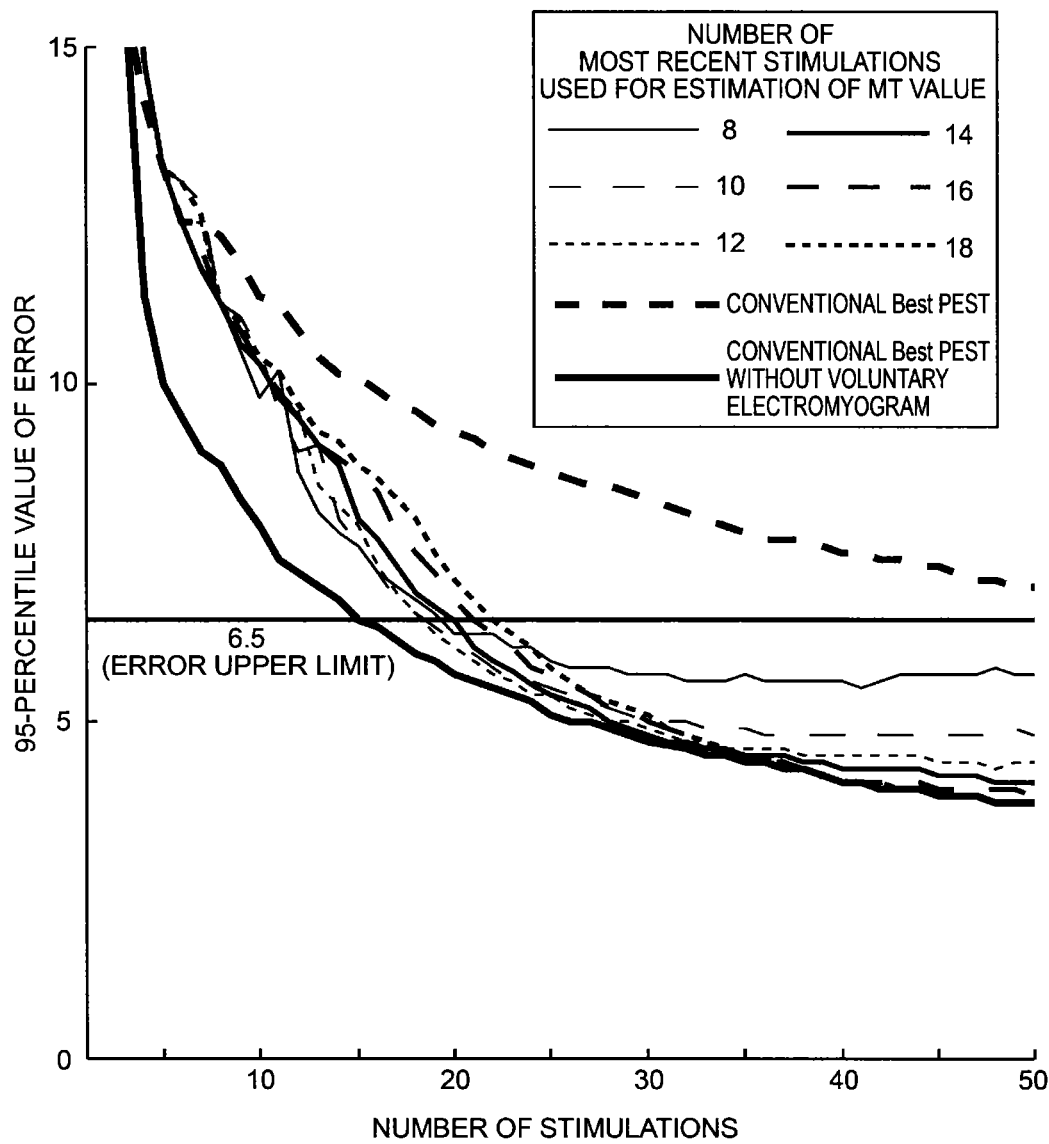

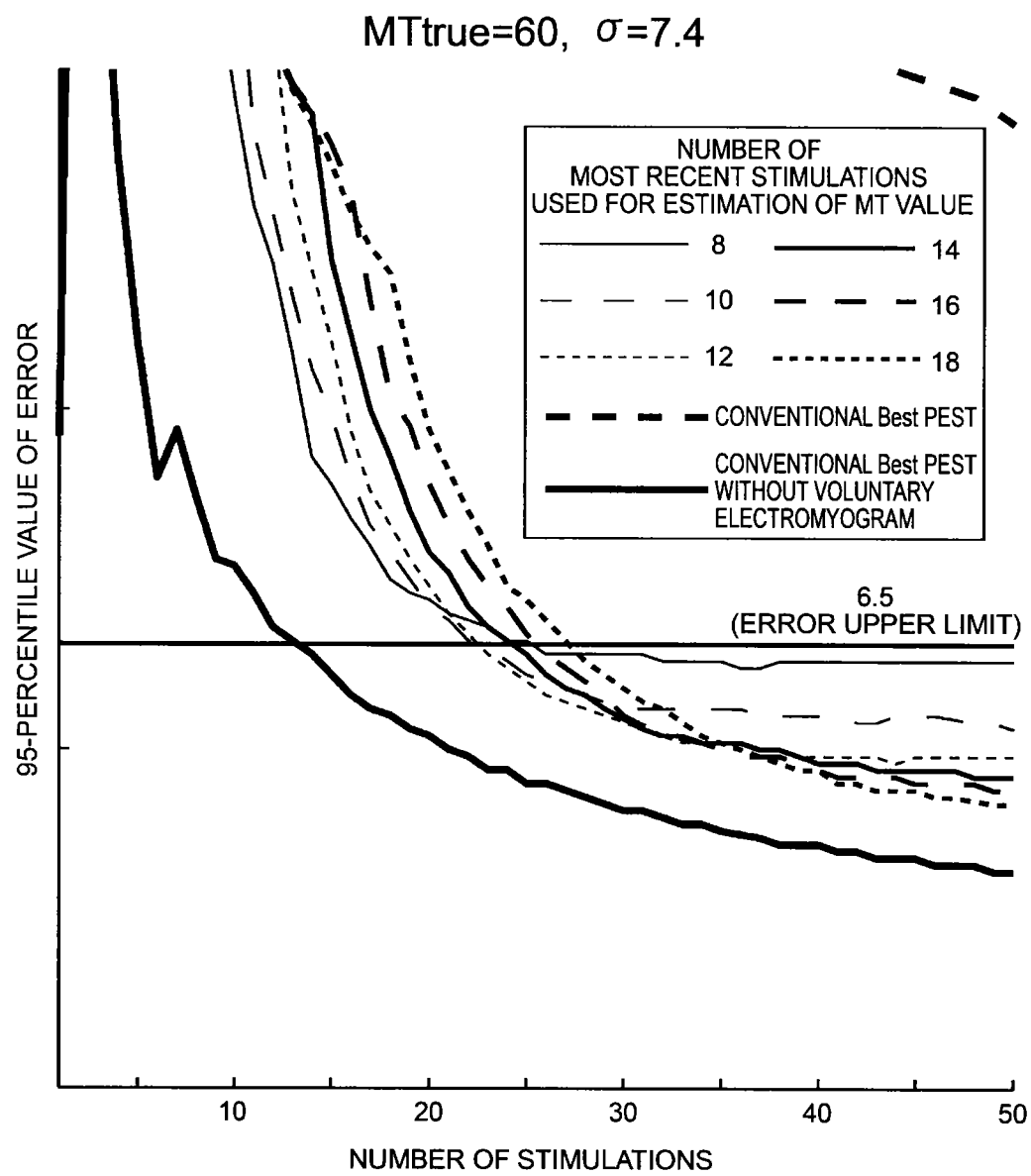

THRESHOLD ESTIMATION APPARATUS, THRESHOLD ESTIMATION METHOD, AND NON-TRANSITORY COMPUTER-READABLE INFORMATION RECORDING MEDIUM

CROSS-REFERENCE TO RELATED APPLICATION

This application claims the benefit of Japanese Patent Application No. 2014-229524 filed on Nov. 12, 2014, and Japanese Patent Application No. 2015-151520 filed on Jul. 31, 2015, the entire disclosure of which is incorporated by reference herein.

BACKGROUND

1. Field of the Disclosure

The present disclosure generally relates to: a threshold estimation apparatus which, in a short time, estimates a threshold of the intensity of stimulation applied to a living subject that is required for evoking a response of the living subject; a threshold estimation method; and a non-transitory computer-readable information recording medium storing a program.

2. Discussion of the Background Art

Conventionally, studies have been conducted on the functional analysis of a living subject by determining a threshold of the intensity of a stimulus applied to the living subject that is required for evoking a response of the living subject (see Patent Literature 1 and Non-Patent Literature 3). Further, there have also been proposed methods of applying the thus determined threshold to rehabilitation (see Non-Patent Literatures 1 and 2).

For example, there are tests being conducted where the presence or absence of a motor evoked potential (MEP) is detected by stimulating the somatosensory and motor cortices of the brain of a rat or the like through electrocorticogram electrodes and measuring the resulting electromyogram potential of the forelimb extensor digitorum muscle or hindlimb soleus muscle and the distribution of the electrodes, that is, thresholds of the stimulus intensity required for MEP to be generated in response to the stimulation at the respective positions of the motor cortex, is thereby determined. Such distribution of thresholds is referred to as "functional brain map". Functional brain maps obtained by electrical stimulation are used in both clinical and basic studies.

Stimulation of a living subject is performed not only by electrical stimulation via an electrode such as an invasive electrode or a non-invasive electrode but also by magnetic stimulation via a coil or the like as well as other electromagnetic stimulation means. In the present disclosure, such an electrode, coil or the like utilized for application of electrical or magnetic stimulation is generally referred to as "stimulator".

For instance, in clinical settings, functional brain mapping is carried out during brain surgery of a patient with seizure or brain tumor by arranging surface electrodes such as epidural electrocorticogram electrodes and applying stimuli via the surface electrodes. For example, a performer of ablative operation refers to a functional brain map and pays attention not to damage any region believed to have a critical function.

Meanwhile, in basic research, functional brain mapping is often carried out by intracortical microstimulation (ICMS) using needle electrodes. For example, electrical stimuli are applied to a restricted area of cortex via needle electrodes and a functional map of motor cortex is prepared based on the muscle action evoked by the stimuli and the stimulus intensity.

Generally speaking, for a deeper analysis of the functions of a living subject, it is necessary to prepare a functional map that represents, in the form of a threshold distribution, how the threshold of the stimulus intensity at which a response can be evoked in the living subject varies depending on the stimulated spots.

In conventional technologies, for example, at least 30 minutes is required to prepare a single functional brain map using 32 electrodes. Coupled with such a long time required for the preparation, it is conventionally believed that a functional brain map is static and does not change with time.

RELATED ART LITERATURE

[Patent Literature 1] National Patent Publication No. 2007-511328

NON-PATENT LITERATURES

[Non-Patent Literature 1] Raffin E, Siebner H R. Transcranial brain stimulation to promote functional recovery after stroke. Curr Opin Neurol. vol. 27, no. 1, p. 54-60, 2014

[Non-Patent Literature 2] Castel-Lacanal E, et al. Induction of Cortical Plastic Changes in Wrist Muscles by Paired Associative Stimulation in the Recovery Phase of Stroke Patients. Neurorehabil Neural Repair. 2009

[Non-Patent Literature 3] Friedemann Awiszus. TMS and threshold hunting. Transcranial Magnetic Stimulation and Transcranial Direct Current Stimulation (Supplements to Clinical Neurophysiology, Vol. 56). p. 13-23. Elsevier Science B.V. 2003

SUMMARY

However, the present inventors, upon examining in basic studies a hypothesis that various functional maps such as functional brain maps can be dynamic and vary depending on time, are making an effort to best use the results of the studies in clinical settings such as the above-described surgery and various rehabilitations. In order to achieve this, it is required to considerably shorten the time required for preparing a functional brain map.

The present disclosure is made to solve the above-described problems and an exemplary object of the present disclosure to provide: a threshold estimation apparatus which, in a short time, estimates a threshold of the intensity of stimulation applied to a living subject that is required for evoking a response of the living subject; a threshold estimation method; and a non-transitory computer-readable information recording medium storing a program for realizing the apparatus and the method using a computer.

In the present disclosure, the threshold estimation apparatus:

sets an initial value of an intensity associated with each of plural stimulators;

selects, from the plural stimulators, a stimulator for which a threshold associated therewith has not been estimated;

stimulates a living subject via the selected stimulator at an intensity associated with the selected stimulator;

detects whether or not the living subject generated a response evoked by the stimulation;

reduces the intensity associated with the selected stimulator if the response was generated, or increases the intensity associated with the selected stimulator if the response was not generated; and if the thus updated intensity associated with each of the plural stimulators satisfies a predetermined convergence condition, estimates a convergence value of the updated intensity associated with each stimulator satisfying the convergence condition as a threshold associated with the stimulator satisfying the convergence condition, wherein, the selection, stimulation, detection, updating, and estimation are repeatedly performed until a threshold associated with each stimulator is estimated for all of the plural stimulators;

when stimulators consecutively selected are:

(a) the same stimulator, a first stimulus is applied via the stimulator and then, after a first stand-by period, a subsequent stimulus is applied via the same stimulator, or (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

According to the present disclosure, the followings can be provided: a threshold estimation apparatus which, in a short time, estimates a threshold of the intensity of stimulation applied to a living subject that is required for evoking a response of the living subject; a threshold estimation method; and a non-transitory computer-readable information recording medium storing a program for realizing the apparatus and the method using a computer.

BRIEF DESCRIPTION OF THE DRAWINGS

A more complete understanding of this application can be obtained when the following detailed description is considered in conjunction with the following drawings, in which:

FIG. 12A is a graph showing the results obtained by, in order to determine the number of convergences at a stimulus intensity of 45, assuming this intensity as true threshold and simulating the minimum number of stimulations required for obtaining the threshold within a desired range of error as an estimation result;

FIG. 12B is a graph showing the results obtained by, in order to determine the number of convergences at a stimulus intensity of 60, assuming this intensity as true threshold and simulating the minimum number of stimulations required for obtaining the threshold within a desired range of error as an estimation result;

DETAILED DESCRIPTION OF THE PREFERRED EMBODIMENT

Figure 1:
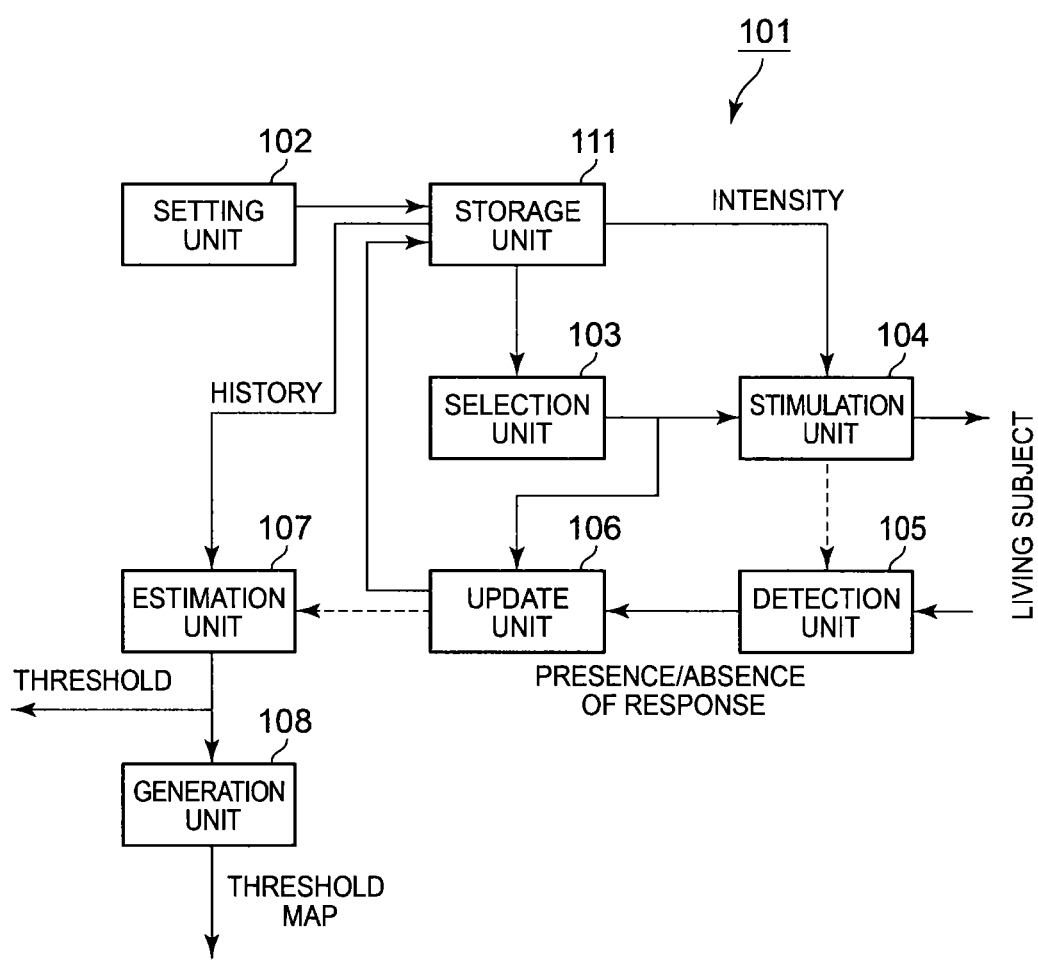
FIG. 1 is a drawing that schematically illustrates the constitution of a threshold estimation apparatus according to one example of the present disclosure.

The exemplary embodiments of the present disclosure will now be described. It should be noted here that the exemplary embodiments are provided for illustrative purposes and do not restrict the scope of the present disclosure. Therefore, those of ordinary skill in the art can adopt an embodiment in which some or all of the elements of any one of the exemplary embodiments are replaced with equivalent counterparts, and the elements described in each example can also be omitted as appropriate in accordance with the intended application. Accordingly, any of such exemplary embodiments constituted in conformity with the principles of the present disclosure are included in the scope of the present disclosure.

Example 1

(Hardware Realizing Threshold Estimation Apparatus)

The threshold estimation apparatus according to the present Exemplary Embodiment is typically realized by a computer executing a program. The computer is connected to various output devices such as stimulators as well as output devices such as electromyography sensors, and exchanges information with these devices.

The program executed by the computer can be distributed and sold through a server to which the computer is connected in a communicable manner, and a non-transitory information recording medium on which the program is recorded, such as a CD-ROM (Compact Disk Read-Only Memory), a flash memory or an EEPROM (Electrically Erasable Programmable ROM), can also be distributed, sold and the like.

The program is installed into the computer's non-transitory information recording medium such as a hard disk, solid-state drive, flash memory or EEPROM. This allows the computer to embody an information processor in the present Exemplary Embodiment. Generally speaking, a CPU (Central Processing Unit) of a computer, which is under the control of the computer's OS (Operating System), reads out a program from an information recording medium to a RAM (Random Access Memory) and then interprets and executes the codes contained in the program. However, in such an architecture where an information recording medium can be mapped within a CPU-accessible memory space, definite loading of the program to the RAM is not always necessary.

Here, the various information required in the program execution process can be temporarily recorded in the RAM.

Alternatively to the use of a general-purpose computer for realizing the information processor of the present Exemplary Embodiment, it is also possible to use a special electronic circuit to configure the information processor of the present Exemplary Embodiment. In this mode, a program can also be utilized as a material for generating a wiring diagram, timing chart and the like of the electronic circuit. In such a mode, an electronic circuit satisfying the specifications defined by the program is formed by an FPGA (Field Programmable Gate Array) or ASIC (Application Specific Integrated Circuit), and the electronic circuit functions as a special instrument that fulfills the functions defined by the program, thereby realizing the information processor of the present Exemplary Embodiment.

To facilitate understanding, the threshold estimation apparatus will now be described postulating a mode in which the threshold estimation apparatus is realized by a computer executing a program.

(Constitution of Threshold Estimation Apparatus)

FIG. 1 is a drawing that schematically illustrates the constitution of a threshold estimation apparatus according to one example of the present disclosure. As shown in FIG. 1, a threshold estimation apparatus 101 includes a setting unit 102, a selection unit 103, a stimulation unit 104, a detection unit 105, an update unite 106, an estimation unit 107, and a storage unit 111. The threshold estimation apparatus 101 may further include a generation unit 108 as an omittable element.

The threshold estimation apparatus 101 is connected to plural stimulators used for stimulating a living subject. The following descriptions assume that plural invasive electrodes arranged in a mesh form are used as the stimulators; however, mesh-form non-invasive stimulation electrodes and coils for magnetic stimulation can also be used as the stimulators.

The threshold estimation apparatus 101 controls at which intensity a living subject should be stimulated via which electrode.

The setting unit 102 sets an initial value of the intensity associated with each of the plural electrodes. Typically, CPU of a computer functions as the setting unit 102.

The thus set initial value of the intensity associated with each electrode is stored in the storage unit 111. Further, as described below, the intensity set for each electrode is updated as the processing proceeds, and the update history thereof is also stored in the storage unit 111. Typically, the storage unit 111 is realized by RAM of a computer. The update history is stored in the form of a sequence, queue or the like.

As described below, the threshold estimation apparatus 101 aims at estimating the thresholds associated with each of the plural electrodes. Therefore, for each electrode, information on whether or not the threshold estimation is completed as well as the threshold obtained by completion of the estimation are also stored in the storage unit 111.

The selection unit 103 selects, from the plural electrodes, an electrode(s) for which threshold associated therewith has not been estimated. Typically, CPU of a computer functions as the selection unit 103. When there is left only one electrode for which threshold has not been estimated, the same electrode is selected consecutively; however, in any other cases, it is desired that such electrodes be randomly selected so that the same electrode or electrodes stimulating neighboring sites are not frequently and consecutively selected.

Meanwhile, the stimulation unit 104 stimulates a living body at an intensity associated with each selected electrode via the selected electrode. Typically, CPU of a computer functions as the stimulation unit 104 by controlling the electrodes through an external input-output interface.

The detection unit 105 detects whether or not the living subject generated a response evoked by the applied stimulation. Typically, CPU of a computer functions as the detection unit 105 by controlling a myogenic potential sensor or the like through an external input-output interface.

The update unit 106 reduces the intensity associated with the selected electrode if the response was generated, or increases the intensity associated with the selected electrode if the response was not generated. Typically, CPU of a computer functions as the update unit 106.

The amount of the increase or decrease in the intensity is most simply a fixed value. For example, the amount of the increase or decrease can be set to be 5% of the maximum intensity applied via the electrode.

Alternatively, the amount of the increase or decrease may be gradually made smaller. For example, the amount of the increase or decrease may be set in such a manner that it is, with respect to the maximum intensity: 10% after a stimulus is applied via the electrode for the first time; 8% after the second stimulation via the electrode; 7% after the third stimulation via the electrode; 6% after the fourth stimulation via the electrode; and uniformly 5% after the fifth stimulation via the electrode.

The updated intensities are added to the history stored in the storage unit 111 for each electrode. That is, in the intensity update history of an electrode that is stored in the storage unit 111, the first element is the initial intensity value of the stimulus applied via the electrode and the last element is the intensity to be used for the next stimulus applied via the electrode.

The estimation unit 107, if the thus updated intensities associated with each of the plural electrodes satisfy a predetermined convergence condition, estimates the convergence value of the updated intensities associated with each electrode satisfying the convergence condition as a threshold associated with the electrode satisfying the convergence condition, For example, when the difference between the largest and smallest values of the immediate (last) five intensities included in the intensity update history of an electrode is within the smallest amount of the increase or decrease by the update (for example, within 5% of the maximum intensity applied via the electrode), it can be judged that the convergence condition is satisfied for the electrode. In the update history, the number of the updated intensity values to be used in the judgment and the value against which the difference between the largest and smallest values is compared can be changed as appropriate in accordance with the intended use.

As a convergence value, for example, the end value of the update history, the value immediately before the end value of the update history, the average or median value of a predetermined number of updated values from the end of the update history, or the intermediate value between the largest and smallest values among a predetermined number of updated values from the end of the update history, can be employed.

The threshold estimation apparatus 101 repeatedly performs the selection by the selection unit 103, the stimulation by the stimulation unit 104, the detection by the detection unit 105, the updating by the update unit 106 and the estimation by the estimation unit 106, until a threshold associated with each electrode is estimated for all of the plural electrodes. This repetition is typically controlled by CPU of a computer.

As described above, the selection unit 103 selects electrodes in such a manner that the same electrode is not consecutively selected as much as possible. When the electrodes consecutively selected by the selection unit 103 are:

(a) the same electrode, a first stimulus is applied via the electrode and then, after a first stand-by period, a subsequent stimulus is applied via the same electrode, or (b) different electrodes, a first stimulus is applied via one of the consecutively selected electrodes that was selected first and then, after a second stand-by period, a subsequent stimulus is applied via the other electrode of the consecutively selected electrodes that was selected later.

Here, the second stand-by period is shorter than the first stand-by period.

Generally speaking, in cases where response of a living subject is observed by consecutively applying the same stimulus in a short time, there is a condition where the response gradually disappears. Thus, when a stimulus is to be applied via the same electrode as the previous one, in order to allow the living subject to forget the previous stimulus, it is required to set aside a sufficiently long first stand-by period.

On the other hand, when a stimulus is to be applied via an electrode different from the previous one, it is believed that the above-described condition is unlikely to occur. In this case, therefore, the time between the present stimulus and the previous stimulus can be set as a second stand-by period, which is shorter than the first stand-by period.

In this manner, in the present Example, by appropriately selecting stimulation electrodes, shortening the time interval between stimuli as much as possible and appropriately setting the amount of the intensity update and the convergence condition, the thresholds associated with the respective electrode can be estimated in a remarkably shorter time than before.

Once the thresholds associated with all of the electrodes are estimated, based on the positions of the plural electrodes and the thus estimated thresholds associated with the respective electrodes, a threshold map representing the distribution of the thresholds is generated.

For example, in a mode where electrocorticogram electrodes arranged above or below the cortical dura mater of the brain of the living subject are used as the electrodes and the detection unit 105 detects the motor evoked potential as a response, the threshold map generated by the generation unit 108 corresponds to a functional brain map representing the localization of the brain functions.

In the related art, it requires about 30 minutes to obtain a single functional brain map using 32 electrodes. On the other hand, in the present Exemplary Embodiment, as described below, the time required for obtaining a single functional brain map is about 4 minutes. Therefore, in the present Exemplary Embodiment, the thresholds associated with the respective electrodes can be estimated in a remarkably shorter time than before.

(Specific Example of Functional Map Preparation)

Figure 2:
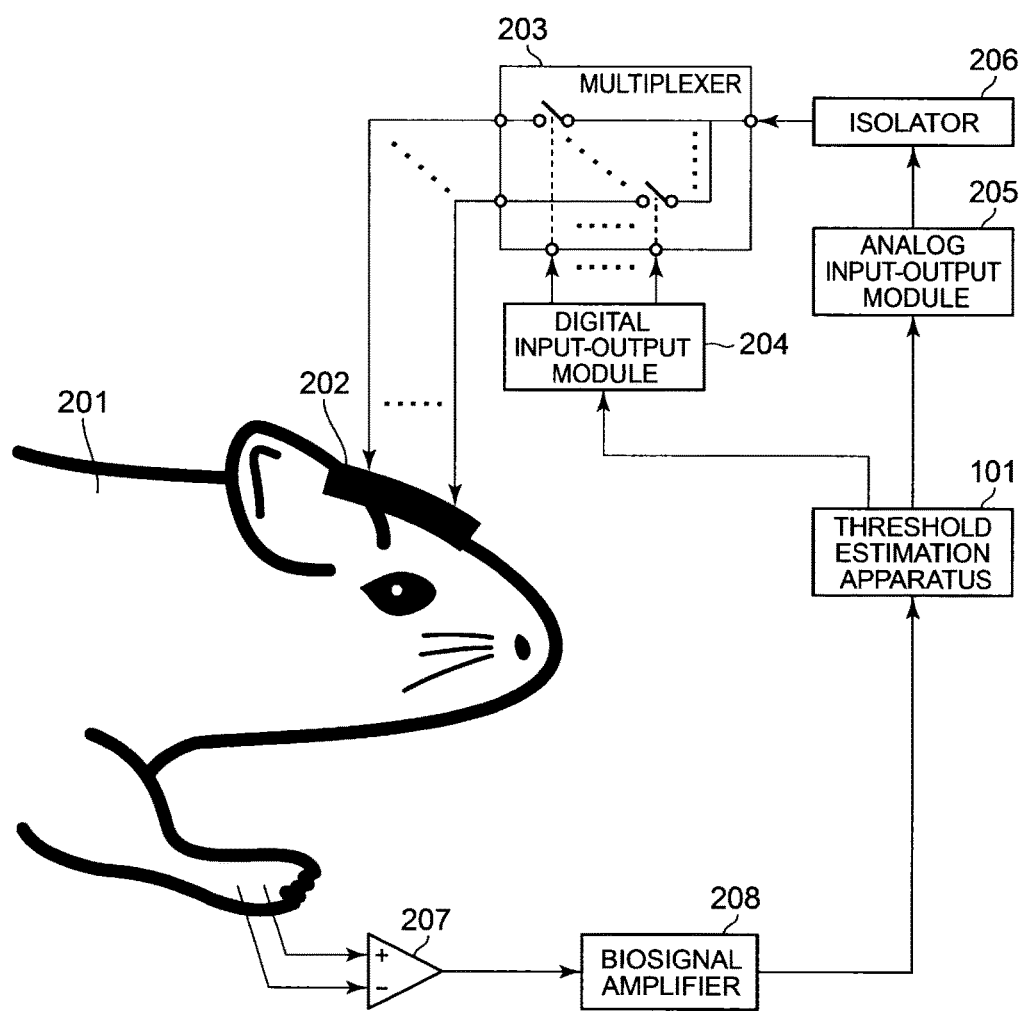
FIG. 2 is a drawing that illustrates a specific example of preparing a functional map.

The processes executed by the threshold estimation apparatus 101 of the present Exemplary Embodiment will now be described referring to a specific example of preparing a functional brain map of cortical motor area. FIG. 2 is a drawing that illustrates the specific example of preparing a functional map.

In this specific example, a rat that belongs to Rodentia and a common marmoset that is a small primate, both of which are widely used as experimental mammals, were employed as living subjects 201.

These living subjects 201 are each stimulated using N-channel electrocorticogram electrodes 202 arranged in an array form. That is, the number of the electrodes is N. The electrodes of the respective channels are hereinafter indicated as ED[0], ED[1], ..., and ED[N−1].

The electrocorticogram electrodes 202 are arranged above or below the cortical dura mater of each living subject 201.

In this Example, one of the electrodes ED[0], ED[1], ..., and ED[N−1] is selected to perform cortical stimulation. For the selection of the electrode, a multiplexer 203 (for example, four ADG406 manufactured by Analog Devices, Inc.) is utilized.

Under instructions from the threshold estimation apparatus 101, the selection pattern of the multiplexer 203 is controlled by a digital input-output module 204 (for example, NI9403 manufactured by National Instruments Corporation), which is isolated from the ground, and switched by a TTL-level digital signal, and one of the electrodes ED[0], ED[1], ..., and ED[N−1] is thereby selected.

Once instruction on the intensity of stimulation current is output from the threshold estimation apparatus 101, an analog input-output module 205 (for example, NI PCIe-6321 manufactured by National Instruments Corporation) outputs a stimulation waveform in an analog signal. Based on this waveform, an isolator 206 (for example, SS-203J manufactured by Nihon Kohden Corporation) generates a stimulation current. In this specific example, the amplitude of 10 consecutive biphasic pulses is instructed by the threshold estimation apparatus 101. Here, since the bipolar pulses are generated at 1 ms intervals, the time length of an electrical stimulation is 10 ms.

The thus generated stimulation current is applied to an input terminal of the multiplexer 203 and then output from the selected electrode. By this, the living subjects 201 are stimulated.

In the living subjects 201, a motor evoked potential is generated when the stimulus intensity is higher than a threshold, while a motor evoked potential is not generated when the stimulus intensity is lower than the threshold. The motor evoked potential detected by a electromyography sensor 207 is band-passed at a frequency band of 1 Hz to 1,000 Hz by a biosignal amplifier 208 (g.USBamp manufactured by G.TEC Medical Engineering GmbH), analog-digital converted at a sampling frequency of 2,400 Hz and then transmitted to the threshold estimation apparatus 101.

The motor evoked potential is generated in about 10-20 ms after stimulation and lasts for about 10 ms. Whether or not a motor evoked potential was generated is determined based on whether or not a post-stimulation change in the myogenic potential occurred with a predetermined amplitude or larger. Therefore, about 40 ms is sufficient for the time length between the initiation of stimulation via an electrode and the completion of the determination of whether or not a motor evoked potential was generated in response to the stimulation.

Figure 4:
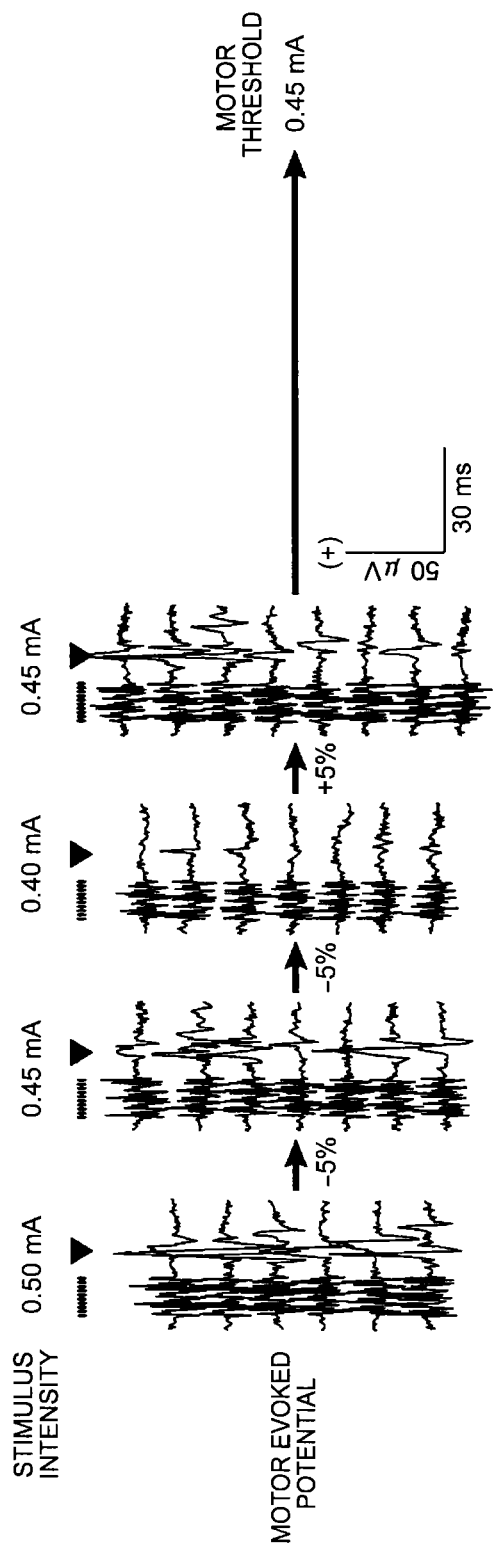
FIG. 4 is a drawing that illustrates a state of estimating a threshold according to a conventional example.

Conventionally, in cases where stimuli are applied to the same spot via the same electrode, it is considered desirable to set aside a period of at least 1 s to 2 s between two stimuli. In the related art, when stimulation of the same spot via the same electrode is performed a predetermined number of times (for example, 7 times to 10 times), among those stimulus intensities that resulted in the generation of motor evoked potential at a predetermined rate or higher (for example, half of the times), the lowest intensity is defined as the threshold. FIG. 4 is a drawing that illustrates a state of estimating a threshold according to a conventional example.

In the example shown in FIG. 4, sequentially:

(a) application of six stimuli at an intensity of 0.50 mA resulted in the generation of MEP all six times, (b) application of seven stimuli at an intensity of 0.45 mA resulted in the generation of MEP six times, (c) application of seven stimuli at an intensity of 0.40 mA resulted in the generation of MEP once, and (d) application of eight stimuli at an intensity of 0.45 mA resulted in the generation of MEP six times.

Accordingly, the threshold is estimated to be 0.45 mA.

However, in this method, the completion of the threshold estimation requires at least 28 stimulations. This means that it requires 28 seconds to about 1 minute (28×2 s=56 s≈1 min) to determine the threshold at only one spot. Conventionally, a functional map is prepared by simply applying this method to repeat the steps of arranging an electrode at one spot, determining the threshold and then moving to another spot; therefore, for example, in order to determine the thresholds of 32 spots by applying stimuli at 2-second intervals, a period of about 30 minutes is required.

In the present Exemplary Embodiment, as described below, not only by drastically reducing the number of stimulations required for determining the threshold at one spot but also by contriving the order of stimulating plural spots, the time required for determining the threshold at all of the plural spots can be remarkably reduced.

It is noted here that a desired shortest interval between stimulations at the same spot (which corresponds to "1 s to about 2 s" in the above-described example) is hereinafter referred to as "the first stand-by period". Further, the time length between stimulation of a spot and the completion of the determination of whether or not a living subject generated a response (which corresponds to "about 30 ms" in the above-described example) is hereinafter referred to as "the second stand-by period". Generally, the second stand-by period is shorter than the first stand-by period.

(Processing in Threshold Estimation Apparatus)

Figure 3:
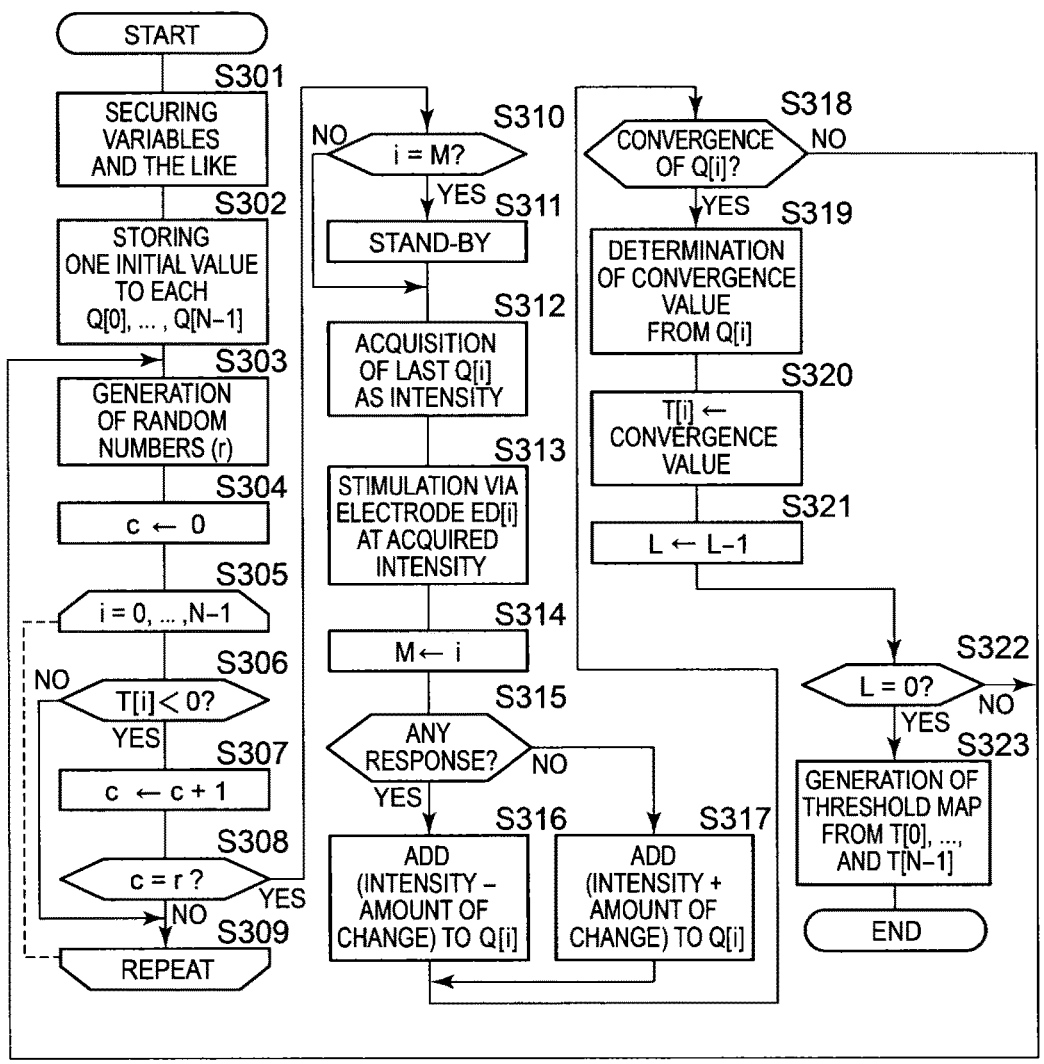
FIG. 3 is a flow chart that illustrates the flow of processes executed by the threshold estimation apparatus.

FIG. 3 is a flow chart that illustrates the flow of processes executed by the threshold estimation apparatus. The following descriptions are provided referring to FIG. 3. It is noted here that, in the data structure and the control sequence shown in FIG. 3, an addition, modification, replacement, omission and the like can be made as appropriate.

Once the processing begins, CPU secures the followings in a RAM: threshold queues $Q[0]$, $Q[1]$, ..., and $Q[N-1]$ associated with the respective electrodes $ED[0]$, $ED[1]$, ..., and $ED[N-1]$; outcome variables $T[0]$, $T[1]$, ..., and $T[N-1]$, which should contain the estimated thresholds; an incomplete variable L, which contains the number of thresholds that have not been estimated; and an ID number variable M of the electrode used for the last stimulation. The queues are each initialized to empty; the outcome variables $T[0]$, $T[1]$, ..., and $T[N-1]$ are initialized to negative values; and the incomplete variable L and the ID number variable M are initialized to N and −1, respectively (Step S301). Here, when an outcome variable $T[i]$ is a negative value, this means that the threshold has not been estimated for an electrode $ED[i]$ and, when the outcome variable $T[i]$ is a non-negative value, this value means the threshold estimated for the electrode $ED[i]$.

Next, the CPU stores appropriate initial values as unique elements for each of the threshold queues $Q[0]$, $Q[1]$, ..., and $Q[N-1]$ (Step S302). As each initial value, an appropriate constant (for example, a half or one-third of the applicable maximum stimulus intensity) may be employed, or an appropriate value may be selected through a preliminary experiment.

Then, the CPU generates random numbers (r), which are non-negative integers smaller than the incomplete variable L (Step S303). In the following descriptions, the random numbers (r) are uniform random numbers; however, as described later, a variety of random numbers can be utilized in the present Exemplary Embodiment.

The CPU subsequently initializes a temporary variable (c) to 0 (Step S304), and repeats the following processes while sequentially increasing a temporary variable (i) from 0 to N−1 (Step S305). That is, if $T[i]$ is a negative value (Step S306: Yes), the CPU increases the value of (c) by 1 (Step S307) and, if the value of (c) is equal to (r) (Step S308: Yes), the CPU proceeds to Step S310 without repeating these steps. Meanwhile, if the $T[i]$ is a non-negative value (Step S306: No) or the value of (c) is not equal to (r) (Step S308: No), the CPU continues to repeat these steps (Step S309).

Once these repeating processes are completed, the CPU checks if the temporary variable (i) is equal to the ID number variable M (Step S310) and, if these variables are equal (Step S310: Yes), after waiting for at least a time length obtained by subtracting the second stand-by period from the first stand-by period (Step S311), the CPU proceeds to Step S312. Meanwhile, if the temporary variable (i) and the ID number variable M are not equal (Step S310: No), the CPU directly proceeds to Step S312. By this process, when stimuli are consecutively applied using the same electrode, a moratorium of the second stand-by period is arranged between the stimuli.

Then, the CPU acquires the last value of the queue $Q[i]$ (Step S312), stimulates the living subject 201 via the electrode $ED[i]$ at an intensity of the thus acquired value (Step S313), and stores the value of (i) in the ID number variable M (Step S314). Subsequently, whether or not the living subject 201 showed a response within the first stand-by period after the stimulation is checked (Step S315).

If the living subject 201 showed a response (Step S315: Yes), the CPU enqueues a value, which is obtained by subtracting the amount of change to the value acquired in Step S310, to the queue $Q[i]$ (Step S316), whereas if the living subject 201 did not show a response (Step S315: No), the CPU enqueues a value, which is obtained by adding the amount of change from the value acquired in Step S310, to the queue $Q[i]$ (Step S317).

Here, the added or subtracted amount of change can be a fixed amplitude as described above, or it can be gradually reduced. In this Example, a mode in which the amount of change is a fixed amplitude (5% of the maximum stimulus intensity) is described.

Subsequently, the CPU determines if the queue $Q[i]$ satisfies the convergence condition (Step S318). For the determination of whether or not the convergence condition is satisfied, various modes can be employed as described above; however, in this Example, as long as the difference between the maximum and minimum values of a predetermined number (for example, 5) of last elements of the queue $Q[i]$ is within the amount of change, it is judged that the convergence condition is satisfied with respect to the electrode $ED[i]$.

If the convergence condition is not satisfied (Step S318: No), the CPU returns its control back to Step S303. Meanwhile, if the convergence condition is satisfied (Step S318: Yes), the CPU determines the convergence value from the queue $Q[i]$ (Step S319), stores the thus obtained convergence value in the outcome variable T[i] (Step S320) and then reduces the incomplete variable L by 1 (Step S321).

In a method of determining the convergence value from the queue Q[i], as described above, for example, (a) the end value of the queue Q[i] (the intensity of a stimulus to be applied next), (b) the value immediately before the end of the queue Q[i] (the stimulus intensity of the last stimulation), (c) the average value of a predetermined number (for example, 5) of the last elements of the queue, (d) the median value of a predetermined number (for example, 5) of the last elements of the queue, or (e) the intermediate value between the largest and smallest values among a predetermined number (for example, 5) of the last elements of the queue can be employed.

In the above-described control, whether or not the convergence condition is satisfied is determined after the update of adding the next stimulus intensity for the ED[i] to the queue Q[i]; however, this order may be reversed as appropriate.

Figure 5:
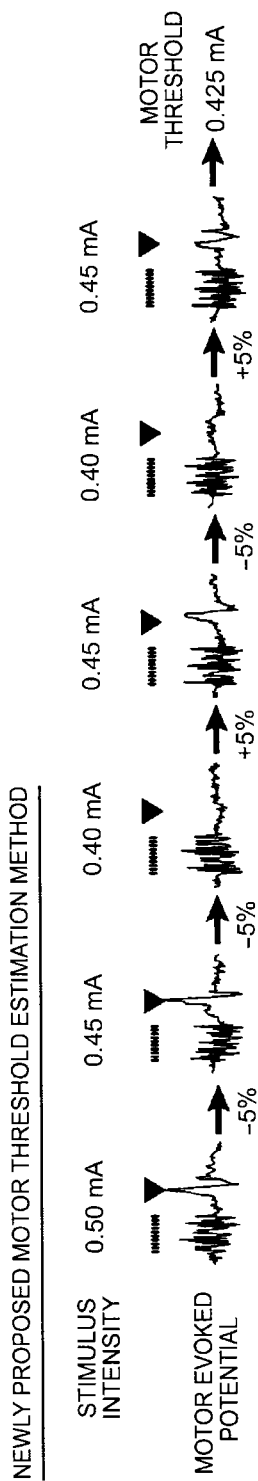
FIG. 5 is a drawing that illustrates the state of estimating a threshold according to the present Exemplary Embodiment.

FIG. 5 is a drawing that illustrates the state of estimating a threshold according to the present Example. In FIG. 5, a response was generated at an initial stimulus intensity of 0.50 mA; a response was generated even when the stimulus intensity was reduced to 0.45 mA; no response was generated at a further reduced stimulus intensity of 0.40 mA; a response was, however, generated when the stimulus intensity was restored to 0.45 mA; no response was generated when the stimulus intensity was reduced again to 0.40 mA; and a response was generated when the stimulus intensity was restored to 0.45 mA. Therefore, the convergence condition is satisfied in mere six stimulations. Also, the median value of 0.45 mA and 0.40 mA, which is 0.425 mA, is defined as the convergence value.

Thereafter, if the incomplete variable L is 0 (Step S322: Yes), the CPU generates a threshold map based on the thresholds obtained as the outcome variables T[0], T[1], . . . , and T[N−1] (Step S323), thereby completing the present processing. Meanwhile, if the incomplete variable L is not 0 (Step S322: No), the CPU returns its processing back to Step S303.

The term "threshold map" used herein refers to a distribution map that depicts the associations between the positions of the electrodes E[0], E[1], . . . and E[N−1] and the threshold values obtained as the outcome variables T[0], T[1], . . . and T[N−1].

Figure 6:
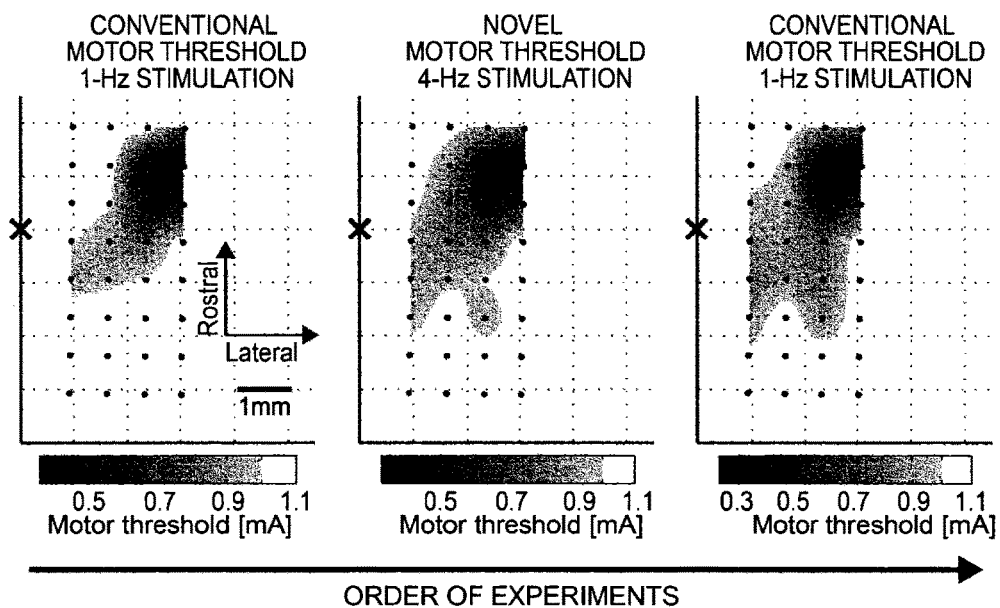
FIG. 6 shows concentration-based threshold maps obtained by applying a conventional method and the present Exemplary Embodiment to a rat.
Figure 7:
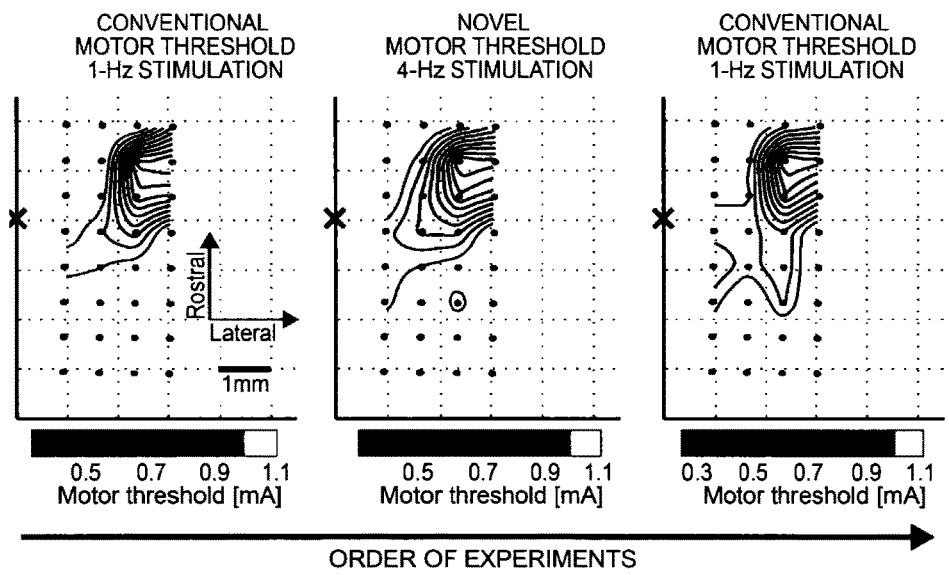
FIG. 7 shows contour-based threshold maps obtained by applying a conventional method and the present Exemplary Embodiment to a rat.
Figure 8:
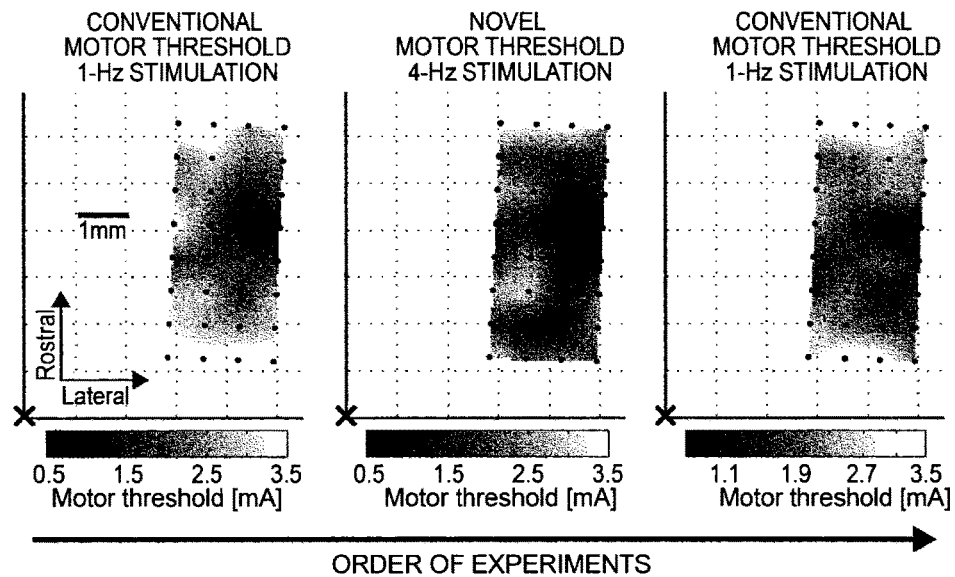
FIG. 8 shows concentration-based threshold maps obtained by applying a conventional method and the present Exemplary Embodiment to a marmoset.
Figure 9:
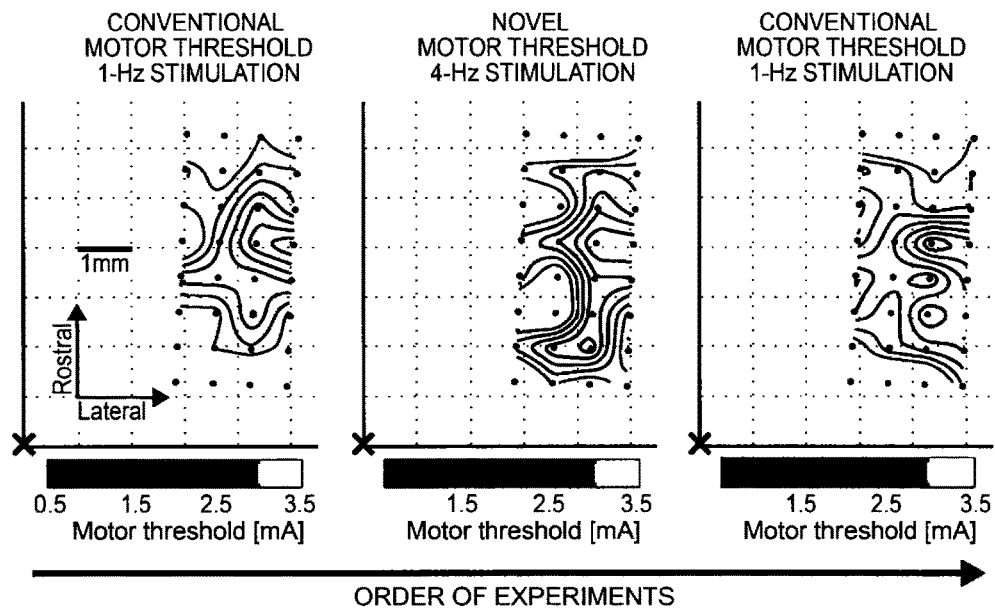
FIG. 9 shows contour-based threshold maps obtained by applying a conventional method and the present Exemplary Embodiment to a marmoset.

FIG. 6 shows concentration-based threshold maps obtained by applying a conventional method and the present Exemplary Embodiment to a rat. FIG. 7 shows contour-based threshold maps obtained by applying a conventional method and the present Exemplary Embodiment to a rat. FIG. 8 shows concentration-based threshold maps obtained by applying a conventional method and the present Exemplary Embodiment to a marmoset. FIG. 9 shows contour-based threshold maps obtained by applying a conventional method and the present Exemplary Embodiment to a marmoset. The following descriptions are provided referring to these figures.

These threshold maps show the experimental results for comparing the conventional example and the present Exemplary Embodiment. In the experiments of the conventional example, the stimulation interval is 1 s (1 Hz). Meanwhile, in the experiments of the present Exemplary Embodiment, the first stand-by period is 1 s (1 Hz) and the second stand-by period is 0.25 s (4 Hz). It is noted here that, as described below, the first and second stand-by periods can both be further shortened.

A threshold map is prepared first according to the conventional example and then according to the present Exemplary Embodiment. Thereafter, another threshold map is prepared according to the conventional example so as to show the transition.

As seen from these figures, the threshold maps obtained by the conventional example and those obtained by the present Exemplary Embodiment show strong correlations. In the rat experiments, the degree of correlation was 0.87±0.13 for the motor cortex forelimb area and 0.80±0.13 for the motor cortex hindlimb area. In the marmoset experiments, the degree of correlation was about 0.66.

In addition, the number of stimulations required for estimating the threshold at one spot was 48±15 in the conventional rat example using a rat; however, it was drastically reduced to 12±13 in the present Exemplary Embodiment. Further, for inhibition of plastic change caused by the motor cortex stimulations, the stimulation interval could not be set at less than 1 s in the conventional example; however, in the present Exemplary Embodiment, the first stand-by period could be set at 0.25 s. It is seen, therefore, that the time required for preparing a whole threshold map can be reduced to about one-sixteenth in the present Exemplary Embodiment.

Figure 10:
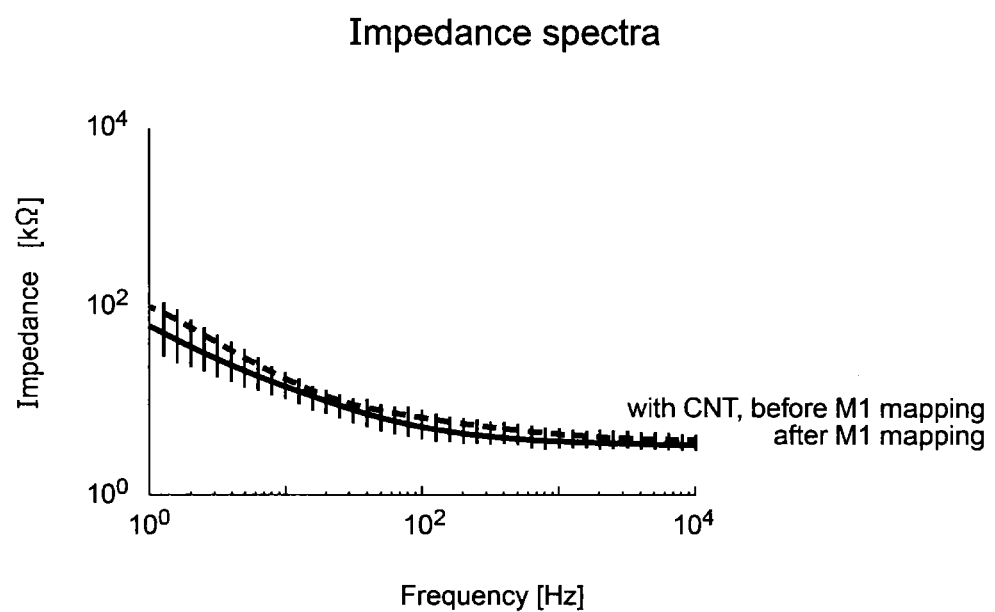
FIG. 10 is a graph showing the changes in electrode impedance in the repeated measurement of threshold maps.

Next, the effect of the simulation performed for preparing a threshold map on the electrode impedance was examined. FIG. 10 is a graph showing the changes in impedance when plural threshold maps were produced. In the graph shown in FIG. 10, the abscissa represents the frequency of generating a threshold map and the ordinate represents the value of electrode impedance.

This graph shows two lines with different color densities. The black line (lower line) represents the average impedance of 32 electrodes prior to the generation of threshold maps. The gray line (upper line) represents the average impedance of 32 electrodes after the generation of 100 threshold maps according to the present Example.

It is generally known that, since a stimulating act causes electrolysis of the electrode material, plural stimulating events largely increases the electrode impedance to impair the measurement performance of electrodes. This means that it is extremely difficult to satisfactorily perform both an stimulating act, that is, determination of an output map, and an activity-recording act, that is, determination of an input map.

Meanwhile, in the present Example, it is seen that, because the number of stimulations required for generating a threshold map is limited, even if a large number of threshold maps are generated, the electrode impedance stays low and the electrode deterioration is small. In the below-described determination of output and input maps, electrodes are utilized for stimulation as well as measurement of electric potential, and it is seen that these can both be satisfactorily performed according to the present Example.

Further, by numerical experiments, the usefulness of this method was verified. A living subject is simulated, assuming that the probability of MEP to be generated in response to a stimulus of an intensity (m), p(m,MT,σ), has a true threshold (MT) as its average value and conforms to a normal distribution whose dispersion is represented by $\sigma^2$. That is, the probability is represented as:

$$p(m,MT,\sigma)=\int_{-\infty}^{m}\exp(-[(x-MT)^2/(2\sigma^2)])dx/[\sigma(2\pi)^{1/2}]$$

and uniform random numbers (r) between 0 and 1 are generated. When p(m,MT,σ) is not less than (r), it is determined that MEP was generated in response to a stimulus of an intensity (m), whereas when p(m,MT,σ) is less than (r), it is determined that no MEP was generated in response to a stimulus of an intensity (m).

The living subject was simulated in the above-described numerical experiment model where MT=60 and σ=4.2 and, by performing the numerical experiments to observe its response to stimuli consecutively given at one spot and applying thereto the conventional example and the present Example, the true MT value was estimated.

As a result, in the conventional example, an estimated value was obtained with a number of stimulations of 44.9±7.7, and the relative error of the estimated value was 6.7±3.4%.

Meanwhile, in the above-described mode, an estimated value was obtained with a number of stimulations of 11.6±6.4, and the relative error of this estimated value was 5.6±3.2%.

From these results as well, it is seen that, according to the present method, at a reliability of not less than 0.999, the number of stimulations can be reduced to about one-fourth and the estimation can be performed with small error.

Furthermore, in the above-described experiments, the present method can use a stimulation frequency that is about four times as high as that of the conventional example. From these experiments, it was found that the time required for the estimation of threshold in the present method is about one-sixteenth of that in the conventional example.

It is believed that the data in the above-described experimental results can be further optimized, and it is also possible to shorten the first stand-by period and/or the second stand-by period in accordance with the characteristics of the living subject 201. For example, by setting the second stand-by period to be about 50 ms to 100 ms (10 Hz to 20 Hz), the generation of a threshold map can be further accelerated.

Generally speaking, in the measurement of a response shown by a living subject, in order to be able to distinguish whether a stimulus was directly detected by a sensor or the living subject responded to the stimulus, it is required to define the time length of a stimulus, $T_A$, and the time interval between the end of a stimulus and the start of the next stimulus, $T_B$. Accordingly, the second stand-by period is, at the shortest, $T_A+T_B$.

In this manner, according to the present Example, a threshold map can be prepared considerably faster than before.

It is noted here that, in the above-described experimental examples, the motor cortex of each living subject 201 was used as the site to be stimulated and the response thereto was measured in terms of MEP. However, stimulations can be applied to any site as long as the presence or absence of a response can be detected.

For example, a mode in which the speech area of a person is stimulated and a voice generated by the person is detected as a response is considered. In this case, the existing measurement and analytical technologies in sound processing can be suitably used to perform, for example, acquisition of the voice through a microphone and subsequent spectral analysis.

In addition, the present Example can also be applied to a mode in which the sensory cortex of a person is stimulated and the person is asked to report the sensation that he or she felt.

For example, when a stimulus is applied to the visual cortex of a person, the person sees an image corresponding to the stimulus. Thus, by asking the person to describe the image in words and systematizing the reported results, a functional map of the visual cortex can be prepared.

The tested person is asked to verbally report the sensation in accordance with the subject function of the visual-related cortex by, for example, indicating the spatial coordinates (position) within the field of vision where the person sees a light or verbally describing the shape and the color of the image.

By applying this method, impressions that a person receives from stimulation applied to various senses including the five senses of sight, hearing, smell, taste and touch as well as the sense of equilibrium can be treated as responses.

Here, when the association cortex governing higher-order brain functions is stimulated, it is believed difficult to physically measure a response to the stimulation. However, in the field of cognitive science, studies have been conducted on the techniques of simulatively quantifying a subjective sense by a psychophysical or psychological method. The present Exemplary Embodiment provides an analytical method useful for basic research in such fields.

Further, as the electrodes, not only cortical surface electrodes but also a multi-channel electrode to be inserted deep into the brain can be employed. In the latter case, by preparing a threshold map taking the position and the depth of the electrode into account, a three-dimensional functional brain map can be produced.

The threshold estimation apparatus 101 of the present Example can also be added to, for example, a therapeutic instrument for brain surgery as a plug-in. For instance, in a tumor removal surgery, by applying the present Example, a tumorigenic region can be identified in a short time and the safety can thus be improved.

Example 2

In the above-described Example, the electrode used for applying the next stimulation is selected by generating uniform random numbers; however, the generated random numbers do not have to be uniform.

For example, those electrodes that have not yet passed the second stand-by period after the previous stimulation can all be removed from the selection candidates. In order to do so, a sequence, queue, stack or the like that contains a combination of information on the time of stimulation, the intensity of the applied stimulation and the presence or absence of a response to the stimulation can be prepared and the content thereof may be carefully examined.

Until there is left only a small number of electrodes for which threshold has not been estimated, even if those electrodes that have not yet passed the second stand-by period after the previous stimulation are removed from the selection candidates, there is still a sufficient number of candidate electrodes.

In cases where the number of remaining electrodes for which threshold has not been estimated becomes small and removal of all of the electrodes that have not yet passed the second stand-by period after the previous stimulation from the selection candidates does not leave even one candidate, any one of the electrodes for which threshold has not been estimated can be randomly selected.

Alternatively, random numbers may be generated all at once such that the electrodes are each used the same number of times as much as possible. That is, random numbers are generated all at once as many as the number of the electrodes for which threshold has not been estimated and, with this being taken as a single cycle, the random numbers are sequentially used within this cycle.

Then, once the random numbers are used up and the first cycle is completed, random numbers are again generated all at once as many as the number of the electrodes for which threshold has not yet been estimated, and this is taken as the next cycle. In this manner, the generation of random numbers is repeated cycle by cycle.

In the case of performing such cycle-by-cycle processing, rather than using random numbers to manage the number of the electrodes for which threshold has not been estimated and the like, a method of directly managing the ID numbers of the electrodes for which threshold has not been estimated is also suitably employed. That is, a single cycle is defined as processes of initially storing integers of 0 to N−1 in a sequence, queue or list of the ID numbers of the electrodes for which threshold has not been estimated, randomly shuffling the elements of the sequence or the like utilizing a library function and using the electrodes sequentially in the order of the elements stored in the sequence or the like.

Once the cycle is completed, the ID numbers of those electrodes for which threshold has now been estimated are deleted from the sequence or the like and, after again randomly shuffling the elements of this sequence or the like, the processing is repeated. When the sequence or the like becomes empty, it means that the threshold has been estimated for all of the electrodes.

This method is capable of reducing the probability that the same electrode is used consecutively.

Further, as a stand-by period for removing certain electrodes from the selection candidates, a time length other than the second stand-by period may be employed as well. For example, a third stand-by period arranged between the first and second stand-by periods can be employed as the stand-by period for removing electrodes from the selection candidates.

Example 3

In the above-described Examples, a threshold map is generated in a short time at a certain time point; however, by repeating this process, the dynamically changing state of the functional brain map can be observed.

Figure 11:
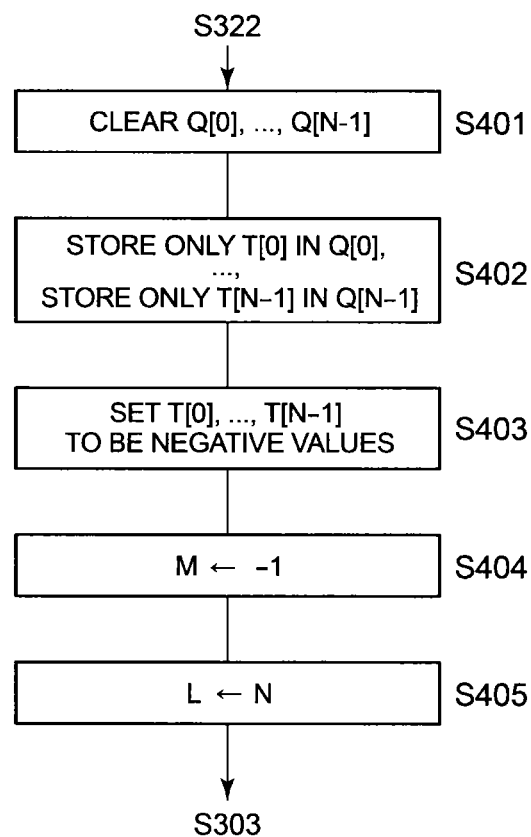
FIG. 11 is a flow chart that illustrates the flow of processes for determining the temporal change of a threshold map.

FIG. 11 is a flow chart that illustrates the flow of processes for determining the temporal change of a threshold map. The following descriptions are provided referring to FIG. 11. It is noted here that the descriptions of those parts that are the same in the above-described processing will be omitted as appropriate.

That is, in this processing, after a threshold map is prepared (Step S322), the CPU deletes the queues Q[0], Q[1], . . . and Q[N−1] (Step S401) and stores each of the previously estimated thresholds T[0], T[1], . . . and T[N−1] as a unique element of each of the queues Q[0], Q[1], . . . and Q[N−1] (Step S402). Then, the CUP sets the outcome variables T[0], T[1], . . . and T[N−1] to be negative values (Step S403); sets the ID number variable M to be −1 (Step S404); sets the incomplete variable L to be N (Step S405); and then returns the control back to Step S303.

According to this mode, functional maps are generated sequentially and, by arranging the thus obtained functional maps in the order of time, the dynamic changes of a functional brain map that occur in minutes can be revealed. This was made possible for the first time because of the studies conducted by the present inventors.

Example 4

In the above-described Examples, the electrodes are used for stimulation; however, the electrodes themselves can also be utilized for measuring and recording.

For example, during the period between the preparations of threshold maps (between Step S322 and Step S401 in the above-described Example), no stimulation is applied by any of the electrodes. Thus, at this stage, the electric potential of each electrode is measured. Then, an observation map, in which the electrode positions are associated with the electric potential measured at the respective positions, is generated.

Each electrode is connected to a switching circuit which determines if the electrode is used for stimulation or the electrode is used as a terminal for measuring the electric potential. The threshold estimation apparatus 101 amplifies the electric potential using a biosignal amplifier, which is connected to the electrodes at the time of measurement, and performs analog-digital conversion, thereby the electric potential values at the respective positions can be obtained in an input map.

In this manner, a threshold map and an observation map are repeatedly obtained. These represent the temporal changes in the brain functions between an output map and an input map.

It is believed that, by applying new stimulation in an intervening manner in addition to the stimulation applied for generating a threshold map while verifying the temporal changes, changes in the sensory properties can be induced in rehabilitation and the like. Examples of the new stimulation that can be used include: new stimulation applied via an electrode used for generating a threshold map (stimulation that is not used for generating a threshold map); a stimulation applied to other part of the living subject through other instrument or the like; a stimulation of pressing or rubbing the surface of the living subject; a stimulation of bending or extending a joint of the living subject from outside; and a visual stimulation provided by display of an image or the like.

For example, by stimulating body parts by massage without using any electrode connected to the threshold estimation apparatus 101 and measuring the electric potential of each spot using the electrodes connected to the threshold estimation apparatus 101, an observation map (input map) representing the activities of the somatosensory cortex can be obtained.

In addition, by applying a visual stimulation with display of an image and measuring the electric potential of each spot using the electrodes connected to the threshold estimation apparatus 101, an observation map (input map) representing the activities of the visual cortex can be obtained.

Meanwhile, by performing stimulation via the electrodes connected to the threshold estimation apparatus 101 in accordance with the above-described Examples, a threshold map (output map) can be obtained.

Therefore, by comparing the temporal changes between an input map and an output map that are obtained from a subject, an examiner is able to verify the brain activities of the subject. This consequently enables to perform an response-adapted therapy where stimulation to be given is adjusted while checking the temporal change of a functional brain map. In other words, by actively intervening in the brain activities by way of stimulation, for example, the effects of rehabilitating the motor, cognitive, language and sensory functions can be facilitated and functional recovery can thereby be induced.

Example 5

The above-described Exemplary Embodiments assume the use of plural electrodes; however, as described above, the principles of the present disclosure can also be applied to a case where a single position is stimulated by a single electrode and the stimulation is used to determine the threshold required for evoking a response.

In this case, since there is only one relevant electrode, the selection process performed by the selection unit 103 and the generation of a threshold map performed by the generation unit 108 can be omitted as appropriate.

In this mode, it is required that the time interval between stimuli applied via the same electrode be about the same as that in a conventional example; however, as compared to a conventional example, the number of stimulations required for determining a threshold can be drastically reduced in this mode. For example, in the above-described experimental example, the number of stimulations is reduced to about one-fourth.

Example 6

As described above, the threshold estimation apparatus 101 based on the principles of the present disclosure is capable of estimating, in a short time and with high frequency, the threshold of the stimulus intensity that evokes a response of a living subject when a certain spot of the subject's brain is stimulated and thereby generating a functional map (threshold map) of a certain region of the brain. Meanwhile, there have been previously proposed rehabilitation methods utilizing an estimated threshold.

In rTMS (Repetitive Transcranial Magnetic Stimulation) disclosed in Non-Patent Literature 1, the motor threshold is estimated for one spot of the cortical region that corresponds to a disabled body part (for example, wrist) of a patient. The term "motor threshold" used herein means the stimulus intensity at which a response is evoked with a probability of 50% when the motor-related brain region is stimulated, and it is substantially the same as a threshold estimated by the threshold estimation apparatus 101. A lower motor threshold means that the patient's brain is in an excited state.

For example, in the case of a patient with stroke, it is considered highly effective to apply natural stimulation by massaging or the like after suppressing an abnormally excited state of the brain.

Accordingly, in rTMS, stimulation for rehabilitation is performed at the one spot for which the motor threshold has been estimated. For example, in order to suppress the excited state, a stimulus weaker than the motor threshold (for example, about 90% to 95% of the motor threshold) is applied. On the other hand, in order to facilitate the excited state, a stimulus stronger than the motor threshold (for example, about 100% to 105% of the motor threshold) is applied.

The stimulation to be applied here is one for rehabilitation that plays a role as one unit of a rehabilitation therapy, not a stimulation applied for the purpose of estimating a threshold.

Thereafter, for the one spot, the motor threshold is estimated again. This yields a motor threshold that is higher or lower than the one previously estimated, depending on the effect of the applied stimulation as well as the condition and symptom of the patient.

As described above, a motor threshold that is higher than the one previously estimated means that the excited state of the patient's brain was suppressed, whereas a motor threshold that is lower than the one previously estimated means that the excited state was facilitated.

For example, the brains of patients with stroke are often in an abnormally excited state. Thus, if the excited stated of the brain was suppressed by the application of the stimulation for rehabilitation, another stimulation for rehabilitation can be applied again in the same manner, but at a slightly weaker intensity than the motor threshold.

Generally speaking, if an application of stimulation for rehabilitation resulted in facilitation of the brain excited state, it is then required to change or adjust the way of applying the stimulation for rehabilitation (for example, stand-by period, stimulus intensity, stimulation time and/or number of stimulations). Accordingly, another stimulation for rehabilitation is applied once again after changing these specifications, or the rehabilitation by this method is terminated at once.

Meanwhile, if an application of stimulation for rehabilitation resulted in suppression of the brain excited state, the stimulation for rehabilitation can be repeated in the same manner as the previous stimulation, or the way of applying the stimulation (for example, stand-by period, stimulus intensity, stimulation time and/or number of stimulations) can be adjusted in such a manner to further improve the level of suppression.

In this manner, by repeating the processes of applying stimulation for rehabilitation and confirming its effect as one unit, the excited state of the brain can be controlled.

As the stimulation for rehabilitation, in addition to stimulation via an electrode, a so-called natural stimulation, for example, a physical stimulation of bending and extending the wrist, can be employed as well. In this case, the intensity of the stimulation for rehabilitation (such as the force applied for bending and extending, the time required for a single round of bending and extending or the number of bending and extending moves) cannot be directly determined from the estimated motor threshold; however, it can be adjusted in the same manner as described above while checking the patient's response.

In rTMS, the above-described processes are repeated; however, by utilizing the threshold estimation apparatus 101 according to the above-described Example, since the time required for threshold estimation is made shorter, the number of stimulations for rehabilitation applied in a certain period of time as well as the number of changes or adjustments made in the stimulation for rehabilitation can be increased. Therefore, as compared to before, superior effects can be obtained by the rehabilitation per unit time and the patent's functional recovery can be further facilitated.

In addition, in rTMS, the stimulation for rehabilitation is performed at only one spot; however, the threshold estimation apparatus 101 according to the above-described Example is capable of generating a functional brain map in a short time.

Therefore, by utilizing the threshold estimation apparatus 101, stimulation for rehabilitation can be performed at multiple spots.

That is, by the threshold estimation apparatus 101, a functional map of the motor cortex corresponding to a disabled body part of a patient is prepared; stimulation for rehabilitation is performed at multiple spots of the motor cortex; and then a functional map is generated again. Thereafter, the operator (including the patient his or herself) compares the two functional maps obtained before and after the stimulation for rehabilitation so as to adjust the next stimulation for rehabilitation to be applied.

In this case, the stimulators used for providing stimulations for the preparation of the functional maps (electrodes or coils) can be directly used for performing the stimulation for rehabilitation.

In PAS (Paired Associative Stimulation) disclosed in Non-Patent Literature 2, for example, for a patient with a disabled wrist, the peripheral nerve of the wrist is stimulated and several tens of milliseconds thereafter, magnetic stimulation is given to one spot of the brain region associated with the peripheral nerve so as to enhance the connection between the peripheral nerve and the spot of the brain region, thereby performing rehabilitation.

As the stimulation applied to the peripheral nerve of the wrist, as in the case of rTMS, stimulation that directly acts on the nerve can be applied via an electrode, a coil or the like, or a so-called natural stimulation, which is a physical stimulation of bending and extending, rubbing, compressing, warming, cooling or the like, can be employed as well.

Meanwhile, from the threshold estimation apparatus 101 according to the above-described Example, an input map (observation map) which shows how the brain responded to the stimulation given to the peripheral nerve of the wrist as well as an output map (threshold map) which shows the intensities of stimuli that should be given to each spot of the brain region for evoking a response of the wrist can be obtained in a short time.

Accordingly, by comparing the input map and the output map and tracking the temporal changes therebetween, in the same manner as in the case of the above-described rTMS, the effects of the rehabilitation can be improved by adjusting:

(a) the type, intensity, time length, number and frequency of the stimulation to be given to a body part (affected part) of a living subject who is in need of rehabilitation;

(b) the intensity, time length, number and frequency of the stimulation to be given at multiple spots of the subject's brain region associated with the affected part; and (c) the length of time that should be waited before applying the next stimulation after once stimulating both the affected part and the brain region associated with the affected part.

In cases where the adjustment of the stimulation for rehabilitation is performed by an operator, it is desired that the threshold estimation apparatus 101 comparatively represent how the patient's threshold, threshold map, observation map and the like changed between before and after the stimulation for rehabilitation which is one unit of a rehabilitation therapy.

This comparison enables the operator to verify the effects of one unit of rehabilitation therapy given to the patient and to thereby adjust each unit of the subsequent rehabilitation therapy.

Example 7

In the above-described Examples, it is assumed that the living subject to be stimulated stays calm during stimulation. For example, in cases where the living subject is a rodent, primate or the like under anesthesia or a human capable of consciously staying calm, the threshold estimation can be carried out with high accuracy even in the above-described Examples.

However, when the subject is an animal in an awake state, the animal may voluntarily generate muscle activity, and this can lead to a reduction in the accuracy of the threshold estimation or an increase in the convergence time.

The present Example is preferred because, by maintaining the intensities of the stimuli applied via each electrode in the past and the history of whether or not a response was evoked by the respective stimuli and updating the intensity referring thereto, even under a poor condition, the estimation accuracy is improved and the convergence time is reduced.

First, the threshold estimation apparatus 101 examines whether or not a response was generated for the most recent stimuli applied by the number of first observations (for example, 4) via each stimulator.

If no response was generated for any of the stimuli, the threshold estimation apparatus 101 increases the stimulus intensity associated with each stimulator by an increment constant. In other words, if no response was generated even for the stimulus applied via a stimulator (i) at an intensity of the end value of the queue Q[i] for the first observations, the threshold estimation apparatus 101 adds a value, which is obtained by adding a predetermined increment value (for example, 10) to the last element of the queue Q[i], to the queue Q[i] as the intensity of the next stimulus applied via the stimulator (i).

If a response was generated for any one of the stimuli, the threshold estimation apparatus 101 then examines whether or not a response was generated for each of the most recent stimuli applied by the number of second observations (for example, 12) via the stimulator (i). It is here assumed that a response was generated at the stimulus intensities of $ms_1$, $ms_2$, ... and $ms_j$, but not at the stimulus intensities of $mf_1$, $mf_2$, ... and $mf_k$. The value of (j+k) is equal to the number of the second observations.

Here, as described above, the probability of MEP to be generated in response to a stimulus of an intensity (m), $p(m,MT,\sigma)$, is considered. It is assumed that the probability $p(m,MT,\sigma)$ has a true threshold (MT) as its average value and conforms to a normal distribution whose dispersion is represented by $\sigma^2$.

Accordingly, the following evaluation function L for an argument parameter μ can be considered:

$$L(\mu,\sigma)=\Sigma_{t=1}^{j}\ln(p(ms_t,\mu,\sigma))+\Sigma_{t=1}^{k}\ln(1-p(mf_t,\mu,\sigma))$$

The threshold estimation apparatus 101 calculates the argument parameter μ that maximizes $L(\mu,\sigma)$ under a constraint of $\sigma=0.07\mu$. The thus calculated argument parameter $\mu_c$ corresponds to the theoretical value of the true threshold. It is noted here that the numerical value of 0.07 in the constraint of $\sigma=0.07\mu$ was defined in accordance with the Best PEST method disclosed in Non-Patent Literature 3 and can be changed as appropriate.

If the thus determined argument parameter $p_c$ is larger than the intensity of the last stimulus applied via the electrode by not less than a predetermined increment value, a value which is obtained by adding the predetermined increment value (for example, 10) to the last element of the queue Q[i] is added to the queue Q[i] as the intensity of the next stimulus applied via the stimulator (i).

Otherwise, the thus determined argument parameter p is added to the queue Q[i] as the intensity of the next stimulus applied via the stimulator (i).

In the above-described Examples, the amount of increase or decrease in stimulation is set to gradually decrease in accordance with the number of stimuli that have been applied; however, in the present Example, a threshold is estimated in accordance with the intensities of recently applied stimuli and the presence or absence of a response thereto, and the intensity of the next stimulus is determined based on the thus estimated value. Therefore, even in such a noise environment where voluntary muscle activity is generated, a more accurate threshold estimation is possible.

In the present Example, as described below, by contriving the convergence condition, the number of stimulations can be reduced. This method can also be applied to the above-described Examples.

That is, in order to satisfy the convergence condition for the stimulator (i), all of the following requirements (a) to (c) must be satisfied:

(a) First, it is required that two stimuli most recently applied via the stimulator (i) have the same intensity;

(b) Secondly, it is required that, for the stimuli most recently applied by the number of first convergences (for example, 5), a response be generated at a predetermined rate or higher (for example, 40%); and (c) Lastly, it is required that stimuli have already been applied via the stimulator (i) by at least the number of convergences that is determined in accordance with the intensity of the last stimulus applied via the stimulator (i).

The term "the number of convergences" used herein refers to the number of stimulations believed to be required for allowing the threshold to be properly estimated based on the intensity of the most recently applied stimulus. Therefore, the number of convergences is determined in accordance with the intensity of the most recently applied stimulus.

The number of convergences can be determined as follows. That is, the number of convergences is determined based on the minimum number of stimulations, which represents the smallest number of stimuli that needs to be applied in order to obtain, as an estimation result, a threshold within an appropriate range of error when a trial of, upon assuming the true threshold, estimating the threshold based on the presence or absence of a response to the stimulation is considered.

Then, based on the number of convergences for the intensity of the most recently applied stimulus, it is judged whether or not stimulations were performed by the number required for proper estimation. Most simply, the minimum number of stimulations can be directly employed as the number of convergences; however, a number that is larger than the minimum number of stimulations can also be employed as the number of convergences. Generally speaking, the higher the intensity of the most recently applied stimulus (assumed true threshold), the larger becomes the number of convergences accordingly. For example, when the most recent stimulus intensity is 45, 60 or 80, the number of convergences can be determined to be 18, 22 or 28, respectively.

Figure 12C:
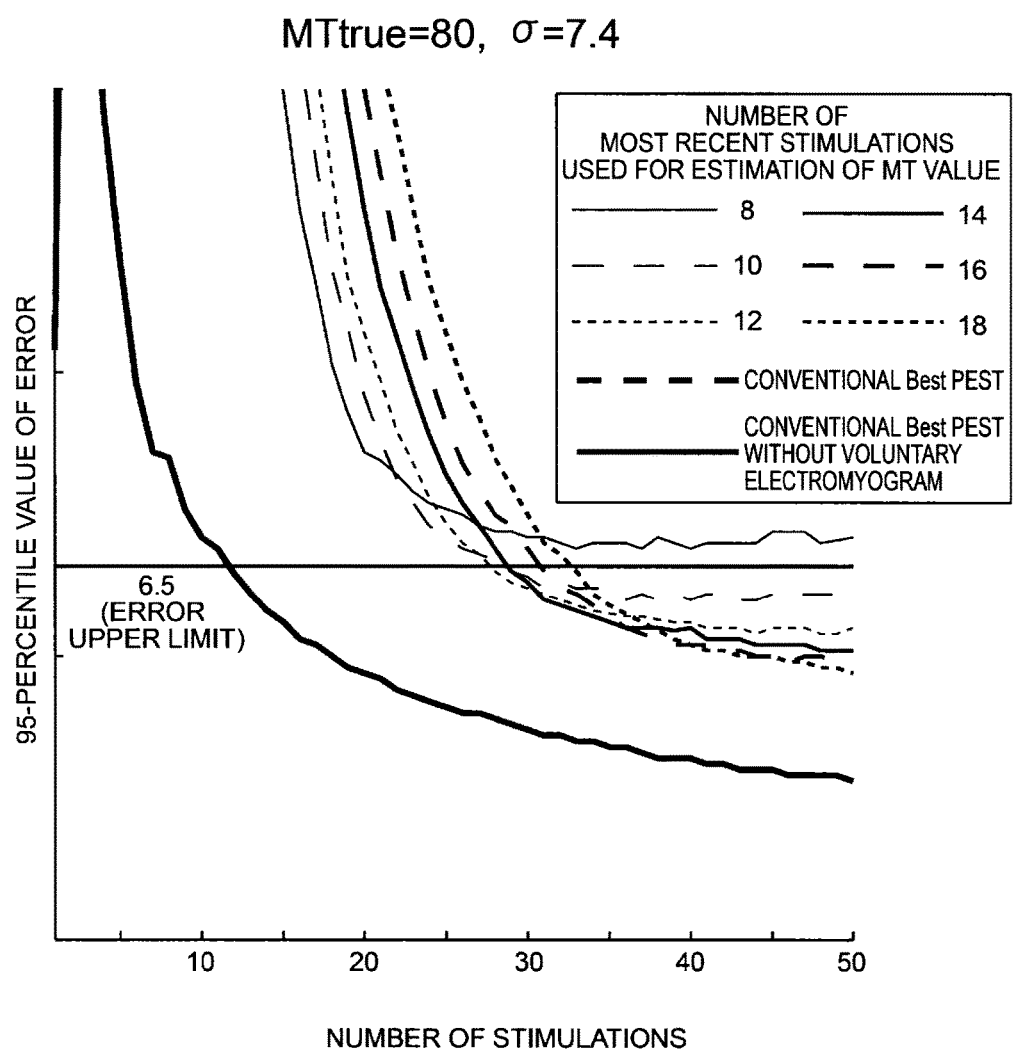
FIG. 12C is a graph showing the results obtained by, in order to determine the number of convergences at a stimulus intensity of 80, assuming this intensity as true threshold and simulating the minimum number of stimulations required for obtaining the threshold within a desired range of error as an estimation result.

In this manner, the number of the second observations and the number of convergences can be determined based on a simulation experiment. FIG. 12A is a graph showing the results obtained by, in order to determine the number of convergences at a stimulus intensity of 45, assuming this intensity as true threshold and simulating the minimum number of stimulations required for obtaining the threshold within a desired range of error as an estimation result. FIG. 12B is a graph showing the results obtained by, in order to determine the number of convergences at a stimulus intensity of 60, assuming this intensity as true threshold and simulating the minimum number of stimulations required for obtaining the threshold within a desired range of error as an estimation result. FIG. 12C is a graph showing the results obtained by, in order to determine the number of convergences at a stimulus intensity of 80, assuming this intensity as true threshold and simulating the minimum number of stimulations required for obtaining the threshold within a desired range of error as an estimation result. The methods of determining the number of the second observations and the number of convergences will now be concretely described referring to these figures.

In the stimulation experiment, with the stimulus intensity (MTtrue), which should be a threshold, being assumed to be 45, 60 or 80 and the a being assumed to represent an average condition at 7.4, the probability of a response to be generated at a stimulus intensity (m), $p(m, MTtrue, \sigma)$, was determined and the threshold was estimated by the Monte Carlo method (10,000 trials) based on the above-described algorithm. Then, the thus estimated threshold and the MTtrue were compared and the 95-percentile values (ordinate) of error in the number of stimulations (abscissa) were calculated. These figures depict their corresponding relationship.

In each trial, uniform random numbers (r) of 0 to 1 were generated and, if an (r) was not less than the value of $\min(0.95, p(m, MTtrue, \sigma))$, it was determined that a response was evoked. Otherwise, it was determined that there was no response.

According to these figures, it is seen that, in the MTtrue range of 45 to 80, the fastest convergence of the 95-percentile of error to an error upper limit of 6.5 or less was obtained when the threshold estimation was performed based on the results of the 12 most recent stimulations. Therefore, the number of the second observations is set to be 12.

Further, when the MTtrue was 45, 60 and 80, the number of stimulations required for the 95-percentile of error to converge to the error upper limit of 6.5 or less was 18, 22 and 28, respectively. Since these values each correspond to the minimum number of stimulations required for the estimation of the respective true thresholds, they are each employed as the number of convergences that corresponds to the respective last stimulus intensities. Moreover, the number of convergences for a stimulus intensity other than these three stimulus intensities can be determined by interpolating the numerical values obtained for these three stimulus intensities. Alternatively, by performing the stimulations while changing the MTtrue as appropriate, the minimum number of stimulations for each stimulus intensity can be determined to thereby determine the number of convergences that corresponds to the stimulus intensity.

As described above, the minimum number of stimulations itself can be employed as the number of convergences; however, for example, by adding several excess stimulations, the estimation accuracy can be improved. The above-described minimum number of stimulations was obtained by determining the 95-percentile of error at $\sigma=7.4$ for each MTtrue and comparing this to the error upper limit of 6.5. Thus, depending on the intended use, the simulations can be carried out by changing these numerical values so as to determine the minimum number of stimulations that conforms to the intended use, and the thus determined minimum number of stimulations or a value obtained by adding several excess stimulations thereto can be used as the number of convergences. The same also applies to the number of the second observations. For example, it is considered to perform stimulations by setting the value of a to be 0.07×MTtrue ($\sigma=0.07 \times MTtrue$) in accordance with the constraint prescribed in the Best PEST method.

It is noted here that these conditions are variable depending on the living subject to be observed. Thus, the conditions can be modified as appropriate in accordance with the living subject. Further, the number of the first observations and the number of the first convergences as well as the proportions with respect thereto can also be defined as appropriate in accordance with the intended use and the like.

Figure 13:
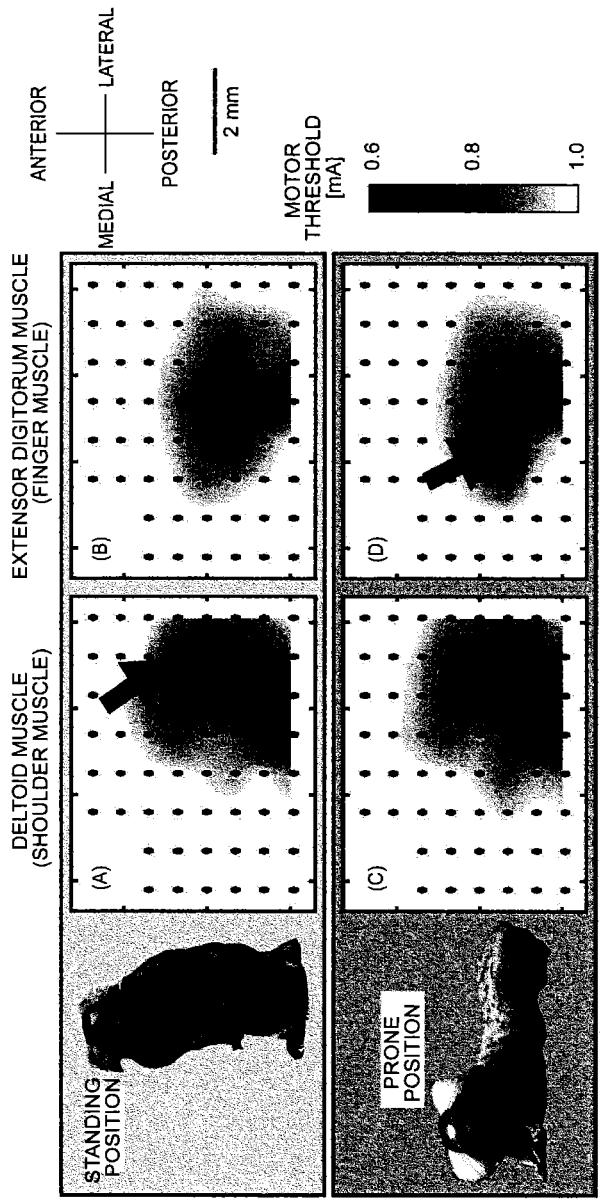
FIG. 13 shows concentration-based threshold maps obtained by applying the present Exemplary Embodiment to marmosets in an awake state.

FIG. 13 shows concentration-based threshold maps obtained by applying the present Exemplary Embodiment to marmosets in an awake state.

In this experiment, 64 stimulation electrodes were chronically placed on the motor area of each marmoset, and the methods of electrical stimulation and threshold estimation according to the present Example were applied to perform functional mapping of the motor cortex in an awake state.

In this experiment, somatotopic maps were obtained for three marmosets at a standing position and a prone position; however, FIG. 13 shows the somatotopic maps obtained for one of the marmosets.

A total of four somatotopic maps are shown in FIG. 13. The maps (A) and (B) were obtained for the marmoset at a standing position, and the maps (C) and (D) were obtained for the marmoset at a prone position. The maps (A) and (C) were obtained for the deltoid muscle (shoulder muscle), and the maps (B) and (D) were obtained for the extensor digitorum muscle (finger muscle).

Comparing these maps, it is seen that the excitability of the primary motor cortex governing the shoulder muscle is significantly higher at a standing position (see the arrow of the map (A)), while the excitability of the primary motor cortex governing the finger muscle is significantly higher at a prone position (see the arrow of the map (D)). That is, the somatotopic map of the primary motor cortex varies in this manner in accordance with the posture of the living subject and, according to the present Example, the dynamic nature of the somatotopic map of the primary motor cortex can be observed.

Further, by repeatedly performing the functional mapping, the pattern of functional brain map that changes every moment can be observed over time.

These results suggest that, for example, even when a large area of the finger-governing region is damaged due to stroke, a change in the posture may potentially allow the undamaged finger-governing region to expand. Therefore, it is believed that, by performing rehabilitation with utilization of the brain function pattern corresponding to the posture while observing the dynamic nature of the somatotopic map of the primary motor cortex according to the present Example, the effects of the rehabilitation can be improved.

SUMMARY

As described above, the threshold estimation apparatus according to the present disclosure is configured such that it includes:

a setting unit that sets an initial value of an intensity associated with each of plural stimulators;

a selection unit that selects, from the plural stimulators, a stimulator for which a threshold associated therewith has not been estimated;

a stimulation unit that stimulates a living subject via the selected stimulator at an intensity associated with the selected stimulator;

a detection unit that detects whether or not the living subject generated a response evoked by the applied stimulation;

an update unit that reduces the intensity associated with the selected stimulator if the response was generated, or increases the intensity associated with the selected stimulator if the response was not generated; and an estimation unit that, if the thus updated intensity associated with each of the plural stimulators satisfies a predetermined convergence condition, estimates a convergence value of the updated intensity associated with each stimulator satisfying the convergence condition as a threshold associated with the stimulator satisfying the convergence condition, wherein, the selection by the selection unit, the stimulation by the stimulation unit, the detection by the detection unit, the updating by the update unit and the estimation by the estimation unit are repeatedly performed until a threshold associated with each stimulator is estimated for all of the plural stimulators;

when stimulators consecutively selected by the selection unit are:

(a) the same stimulator, a first stimulus is applied via the stimulator and then, after a first stand-by period, a subsequent stimulus is applied via the same stimulator, or (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

The threshold estimation apparatus according to the present disclosure can also be configured such that it further includes a generation unit that, based on positions of the plural stimulators and the estimated thresholds associated with the respective stimulators, generates a threshold map representing a distribution of the thresholds.

Further, the threshold estimation apparatus according to the present disclosure can be configured such that the threshold estimation apparatus, after generating the threshold map, deletes an intensity update history associated with each of the plural stimulators, and again performs the repeating process as well as the generation of a threshold map using the estimated thresholds associated with the respective stimulators as initial intensity values associated with the respective stimulators.

Still further, the threshold estimation apparatus according to the present disclosure can be configured such that the threshold estimation apparatus, after generating the threshold map, generates an observation map by measuring, via each of the plural stimulators, electric potentials at positions where the respective stimulators are arranged on a living subject without stimulating the living subject, and again performs the repeating process as well as the generation of a threshold map.

Yet still further, the threshold estimation apparatus according to the present disclosure can be configured such that:

the threshold estimation apparatus stimulates the living subject's brain via the plural stimulators; and the threshold map is a functional brain map.

Yet still further, the threshold estimation apparatus according to the present disclosure can be configured such that the plural stimulators are electrocorticogram electrodes arranged above or below a cortical dura mater of the living subject's brain.

Yet still further, the threshold estimation apparatus according to the present disclosure can be configured such that the detection unit detects a motor evoked potential as the response.

Yet still further, the threshold estimation apparatus according to the present disclosure can be configured such that, the selection unit, if there are, among the plural stimulators, plural stimulators for which a threshold associated therewith has not been estimated, selects such plural stimulators that are different from each other and have passed at least the second stand-by period since being previously selected.

Yet still further, the threshold estimation apparatus according to the present disclosure can be configured such that the selection unit consecutively and randomly selects the different stimulators.

Yet still further, the threshold estimation apparatus according to the present disclosure can be configured such that:

an amount of increase or decrease relating to the intensity update performed by the update unit is a predetermined constant; and when a change in the updated intensity associated with each of the plural stimulators stays within a range of the predetermined constant for a predetermined number of times in a row, the convergence condition is judged to be satisfied for the respective stimulators.

Yet still further, the threshold estimation apparatus according to the present disclosure can be configured such that:

the amount of increase or decrease in the intensity performed by the update unit decreases until reaching the predetermined constant every time an update is made for each of the plural stimulators; and when a change in the updated intensity associated with each of the plural stimulators stays within a range of the predetermined constant for a predetermined number of times in a row, the convergence condition is judged to be satisfied for the respective stimulators.

Yet still further, the threshold estimation apparatus according to the present disclosure can be configured such that the latest intensity associated with a stimulator satisfying the convergence condition is defined as the convergence value for the stimulator satisfying the convergence condition.

Yet still further, the threshold estimation apparatus according to the present disclosure can be configured such that, with respect to a stimulator satisfying the convergence condition, an average value of intensities that stayed within a range of the predetermined constant over the predetermined number of times in a row is defined as the convergence value for the stimulator satisfying the convergence condition.

Yet still further, the threshold estimation apparatus according to the present disclosure can be configured such that, with respect to a stimulator satisfying the convergence condition, a median value of intensities that stayed within a range of the predetermined constant for the predetermined number of times in a row is defined as the convergence value for the stimulator satisfying the convergence condition.

Yet still further, the threshold estimation apparatus according to the present disclosure can be configured such that, for each of the plural stimulators, the update unit:

(a) if the response was not generated for any of stimuli most recently applied via an stimulator by the number of first observations, increases the intensity associated with the stimulator by a predetermined increment constant;

(b) determines an argument parameter that maximizes an evaluation function for threshold based on the intensities of stimuli most recently applied via the stimulator by the number of second observations and the presence or absence of the response for each of the stimuli applied by the number of the second observations and, if the thus determined argument parameter is larger than the intensity of the last stimulus applied via the stimulator by not less than the predetermined increment constant, increases the intensity associated with the stimulator by the predetermined increment constant; and (c) in neither case of the above (a) and (b), updates the intensity associated with the stimulator to the determined argument parameter.

Yet still further, the threshold estimation apparatus according to the present disclosure can be configured such that, for each of the plural stimulators, the convergence condition is satisfied when:

(a) two stimuli most recently applied via a stimulator have the same intensity;

(b) for stimuli most recently applied via the stimulator by the number of first convergences, the response was generated at a predetermined rate or higher; and (c) stimuli have already been applied via the stimulator by at least the number of convergences that is determined in accordance with the intensity of the last stimulus applied via the stimulator.

The threshold estimation method according to the present disclosure is configured such that it includes:

the setting step in which a threshold estimation apparatus sets an initial value of an intensity associated with each of plural stimulators;

the selection step in which the threshold estimation apparatus selects, from the plural stimulators, a stimulator for which a threshold associated therewith has not been estimated;

the stimulation step in which the threshold estimation apparatus stimulates a living subject via the selected stimulator at an intensity associated with the selected stimulator;

the detection step in which the threshold estimation apparatus detects whether or not the living subject generated a response evoked by the applied stimulation;

the updating step in which the threshold estimation apparatus reduces the intensity associated with the selected stimulator if the response was generated, or increases the intensity associated with the selected stimulator if the response was not generated; and the estimation step in which, if the thus updated intensity associated with each of the plural stimulators satisfies a predetermined convergence condition, the threshold estimation apparatus estimates a convergence value of the updated intensity associated with each stimulator satisfying the convergence condition as a threshold associated with the stimulator satisfying the convergence condition, wherein, the selection by the selection step, the stimulation step, the detection step, the updating step and the estimation step are repeatedly performed until a threshold associated with each stimulator is estimated for all of the plural stimulators;

when stimulators consecutively selected in the selection step are:

(a) the same stimulator, a first stimulus is applied via the stimulator and then, after a first stand-by period, a subsequent stimulus is applied via the same stimulator, or (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

The program according to the present disclosure is configured such that the program allows a computer to function as:

a setting unit that sets an initial value of an intensity associated with each of plural stimulators;

a selection unit that selects, from the plural stimulators, a stimulator for which a threshold associated therewith has not been estimated;

a stimulation unit that stimulates a living subject via the selected stimulator at an intensity associated with the selected stimulator;

a detection unit that detects whether or not the living subject generated a response evoked by the applied stimulation;

an update unit that reduces the intensity associated with the selected stimulator if the response was generated, or increases the intensity associated with the selected stimulator if the response was not generated; and an estimation unit that, if the thus updated intensity associated with each of the plural stimulators satisfies a predetermined convergence condition, estimates a convergence value of the updated intensity associated with each stimulator satisfying the convergence condition as a threshold associated with the stimulator satisfying the convergence condition, wherein, the selection by the selection unit, the stimulation by the stimulation unit, the detection by the detection unit, the updating by the update unit and the estimation by the estimation unit are repeatedly performed until a threshold associated with each stimulator is estimated for all of the plural stimulators;

when stimulators consecutively selected by the selection unit are:

(a) the same stimulator, a first stimulus is applied via the stimulator and then, after a first stand-by period, a subsequent stimulus is applied via the same stimulator, or (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

The threshold estimation apparatus according to another exemplary aspect of the present disclosure is configured such that it includes:

a setting unit that sets an initial value of an intensity associated with a stimulator;

a stimulation unit that stimulates a living subject via the stimulator at an intensity associated with the stimulator;

a detection unit that detects whether or not the living subject generated a response evoked by the applied stimulation;

an update unit that reduces the intensity associated with the stimulator if the response was generated, or increases the intensity associated with the stimulator if the response was not generated; and an estimation unit that, if the thus updated intensity associated with the stimulator satisfies a predetermined convergence condition, estimates a convergence value of the updated intensity associated with the stimulator as a threshold associated with the stimulator, wherein, the selection by the selection unit, the stimulation by the stimulation unit, the detection by the detection unit, the updating by the update unit and the estimation by the estimation unit are repeatedly performed until the threshold associated with the stimulator is estimated; and a first stimulus is applied via the stimulator and then, after a first stand-by period, a subsequent stimulus is applied via the stimulator.

The threshold estimation apparatus according to the present disclosure can also be configured such that:

before subjecting the living subject to a single unit of a rehabilitation therapy, the threshold estimation apparatus estimates a threshold of the living subject, which estimated threshold is defined as a pre-intervention threshold;

after subjecting the living subject to the single unit of the rehabilitation therapy, the threshold estimation apparatus again estimates a threshold of the living subject, which estimated threshold is defined as a post-intervention threshold; and the threshold estimation apparatus comparatively presents the pre-intervention threshold and the post-intervention threshold.

INDUSTRIAL APPLICABILITY

According to the present disclosure, a threshold estimation apparatus which, in a short time, estimates a threshold of the intensity of stimulation applied to a living subject that is required for evoking a response of the living subject; a threshold estimation method; and a non-transitory computer-readable information recording medium storing a program for realizing the apparatus and the method using a computer can be provided.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

DESCRIPTION OF SYMBOLS

101 Threshold estimation apparatus
102 Setting unit
103 Selection unit
104 Stimulation unit
105 Detection unit
106 Update unit
107 Estimation unit
108 Generation unit
111 Storage unit
201 Living subject
202 Electrocorticogram electrode
203 Multiplexer
204 Digital input-output module
205 Analog input-output module
206 Isolator
207 Electromyography sensor
208 Biosignal amplifier

What is claimed is:

1. A threshold estimation apparatus including a plurality of stimulators being electrodes or coils applying stimuli respectively to a living subject, the threshold estimation apparatus including a processor and a memory which stores a program executable by the processor, the program comprising:

a setting code that causes the processor to set an initial value of an intensity associated with each of the plurality of stimulators;

a selecting code that causes the processor to select randomly, from the plurality of stimulators, a selected stimulator for which a threshold associated therewith has not been estimated;
a stimulating code that causes the processor to stimulate the living subject via the selected stimulator at an intensity associated with the selected stimulator;
a detecting code that causes the processor to detect whether or not the living subject generated a response evoked by the applied stimulation;
an updating code that causes the processor to update the intensity by reducing the intensity associated with the selected stimulator if the response was generated, or increasing the intensity associated with the selected stimulator if the response was not generated; and
an estimating code that causes the processor to estimate a convergence value of the updated intensity associated with each stimulator as a threshold that satisfies a convergence condition,
wherein,
the selecting code, the stimulating code, the detecting code, the updating code and the estimating code are repeatedly executed by the processor until all thresholds associated with all of the plurality of stimulators are estimated;
when stimulators consecutively selected by the selecting code are:
(a) the same stimulator, a first stimulus is applied via the stimulator and then, after a first stand-by period, a subsequent stimulus is applied via the same stimulator,
(b) when stimulators consecutively selected by the selecting code are different stimulators, a first stimulus is applied via one of the consecutively selected stimulators that was selected first and then, after a second stand-by period, a subsequent stimulus is applied via the other stimulator of the consecutively selected stimulators that was selected later; and
the second stand-by period is shorter than the first stand-by period.

2. The threshold estimation apparatus according to claim 1, further comprising a generating code that causes the processor to generate a threshold map representing a distribution of the thresholds by depicting the thresholds on relative positions of the plurality of stimulators respectively, by concentration or contour.

3. The threshold estimation apparatus according to claim 2, wherein the threshold estimation apparatus, after generating the threshold map, deletes an intensity update history associated with each of the plurality of stimulators, and again performs the repeating process as well as the generation of a threshold map using the estimated thresholds associated with the respective stimulators as initial intensity values associated with the respective stimulators.

4. The threshold estimation apparatus according to claim 3, wherein the threshold estimation apparatus, after generating the threshold map, generates an observation map by measuring, via each of the plurality of stimulators, electric potentials at positions where the respective stimulators are arranged on the living subject without stimulating the living subject, and again performs the repeating process as well as generation of a threshold map.

5. The threshold estimation apparatus according to claim 2, wherein the threshold estimation apparatus stimulates the living subject's brain via the plurality of stimulators; and the threshold map is a functional brain map.

6. The threshold estimation apparatus according to claim 5, wherein the plurality of stimulators are electrocorticogram electrodes arranged above or below a cortical dura mater of the living subject's brain.

7. The threshold estimation apparatus according to claim 5, wherein the detecting is of a motor evoked potential as the response.

8. The threshold estimation apparatus according to claim 1, wherein the selecting code, if there are, among the plurality of stimulators, plural stimulators for which a threshold associated therewith has not been estimated, selects such plural stimulators that are different from each other and have passed at least the second stand-by period since being previously selected.

9. The threshold estimation apparatus according to claim 1, wherein:
an amount of increase or decrease relating to the intensity update is a predetermined constant; and
when a change in the updated intensity associated with each of the plurality of stimulators stays within a range of the predetermined constant for a predetermined number of times in a row, the convergence condition is judged to be satisfied for the respective stimulators.

10. The threshold estimation apparatus according to claim 1, wherein:
the amount of increase or decrease in the intensity performed by the update decreases until reaching the predetermined constant every time an update is made for each of the plural stimulators; and
when a change in updated intensity associated with each of the plurality of stimulators stays within a range of the predetermined constant for a predetermined number of times in a row, the convergence condition is judged to be satisfied for the respective stimulators.

11. The threshold estimation apparatus according to claim 9, wherein, with respect to a stimulator satisfying the convergence condition, an average value of intensities that stayed within a range of the predetermined constant for the predetermined number of times in a row is defined as the convergence value for the stimulator satisfying the convergence condition.

12. The threshold estimation apparatus according to claim 9, wherein, with respect to a stimulator satisfying the convergence condition, a median value of intensities that stayed within a range of the predetermined constant for the predetermined number of times in a row is defined as the convergence value for the stimulator satisfying the convergence condition.

13. The threshold estimation apparatus according to claim 1, wherein, with respect to a stimulator satisfying the convergence condition, a median value of intensities that stayed within a range of a predetermined constant for a predetermined number of times in a row is defined as the convergence value for the stimulator satisfying the convergence condition.

14. The threshold estimation apparatus according to claim 1, wherein, for each of the plurality of stimulators, the updating:
(a) if the response was not generated for any of stimuli most recently applied via a stimulator by the number of first observations, increases the intensity associated with the stimulator by a predetermined increment constant;
(b) determines an argument parameter that maximizes an evaluation function for threshold based on the intensities of stimuli most recently applied via the stimulator by the number of second observations and the presence or absence of the response for each of the stimuli applied by the number of the second observations, and, if the thus determined argument parameter is larger then the intensity of the last stimulus applied via the stimulator by not less than the predetermined increment constant, increases the intensity associated with the stimulator by the predetermined increment constant; and (c) in neither case of the above (a) and (b), updates the intensity associated with the stimulator to the predetermined argument parameter.

15. The threshold estimation apparatus according to claim 1, wherein, for each of the plurality of stimulators, the convergence condition is satisfied when:

(a) two stimuli most recently applied via a stimulator have the same intensity;

(b) for stimuli most recently applied via the stimulator by the number of first convergences, the response was generated at a predetermined rate or higher; and (c) stimuli have already been applied via the stimulator by at least the number of convergences that is determined in accordance with the intensity of the last stimulus applied via the stimulator.

16. A threshold estimation method, comprising:

a setting step in which a threshold estimation apparatus sets an initial value of an intensity associated with each of plural stimulators;

a selection step in which the threshold estimation apparatus selects, from the plural stimulators, a stimulator for which a threshold associated therewith has not been estimated;

a stimulation step in which the threshold estimation apparatus stimulates a living subject via the selected stimulator at an intensity associated with the selected stimulator;

a detection step in which the threshold estimation apparatus detects whether or not the living subject generated a response evoked by the applied stimulation;

a updating step in which the threshold estimation apparatus reduces the intensity associated with the selected stimulator if the response was generated, or increases the intensity associated with the selected stimulator if the response was not generated; and an estimation step in which the threshold estimation apparatus estimates a convergence value of the updated intensity associated with the stimulator as a threshold which satisfies a convergence condition, wherein, the selection by the selection step, the stimulation step, the detection step, the updating step and the estimation step are repeatedly performed until a threshold associated with each stimulator is estimated for all of the plural stimulators;

when stimulators consecutively selected in the selection step are:

(a) the same stimulator, a first stimulus is applied via the stimulator and then, after a first stand-by period, a subsequent stimulus is applied via the same stimulator, or (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

17. A non-transitory computer-readable information recording medium storing a program, allowing a computer to:

set an initial value of an intensity associated with each of the plurality of stimulators, wherein the plurality of stimulators are electrodes or coils applying stimuli respectively to a living subject;

select, from the plurality of stimulators, a stimulator for which a threshold associated therewith has not been estimated;

stimulate the living subject via the selected stimulator at an intensity associated with the selected stimulator;

detect whether or not the living subject generated a response evoked by the applied stimulation;

stimulate the living subject via the selected stimulator at an intensity associated with the selected stimulator;

detect whether or not the living subject generated a response evoked by the applied stimulation;

update the intensity by
  reducing the intensity associated with the selected stimulator if the response was generated, or increases the intensity associated with the selected stimulator if the response was not generated;
  estimating a convergence value of the updated intensity associated with each stimulator as a threshold that satisfies a convergence condition, wherein, the selection step, the stimulation step, the detection step, the updating step and the estimation are repeatedly executed by the computer until a threshold associated with each stimulator is estimated for all of the plurality of stimulators;

when stimulators consecutively selected by the selection unit are:

(a) the same stimulator, a first stimulus is applied via the stimulator and then, after a first stand-by period, a subsequent stimulus is applied via the same stimulator, (b) different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

18. A threshold estimation apparatus including one of circuitry, and a processor and a memory which stores a program executable by the processor, that causes the apparatus to perform logical functions, comprising:

setting an initial value of an intensity associated with each of a plurality of stimulators, wherein the plurality of stimulators are electrodes or coils applying stimuli respectively to a living subject;

selecting randomly, from the plurality of stimulators, a selected stimulator for which a threshold associated therewith has not been estimated;

stimulating the living subject via the selected stimulator at an intensity associated with the stimulator;

detecting whether or not the living subject generated a response evoked by the applied stimulation;

updating the intensity by:

reducing the intensity associated with the selected stimulator if the response was not generated; or increasing the intensity associated with the selected stimulator if the response was not generated; and estimating a convergence value of the updated intensity associated with the stimulator as a threshold which satisfies a predetermined convergence condition, wherein, the selecting, the stimulating, the detecting, the updating and the estimating are repeatedly performed until the threshold associated with each stimulator is estimated for all of the plurality of stimulators; and when stimulators consecutively selected by the selecting are:

(a) the same stimulator, a first stimulus is applied via the stimulator and then, after a first stand-by period, a subsequent stimulus is applied via the same stimulator, (b) when stimulators consecutively selected by the selecting are different stimulators, a first stimulus is applied via one of the consecutively selected stimulators that was selected first and then, after a second stand-by period, a subsequent stimulus is applied via the other stimulator of the consecutively selected stimulators that was selected later; and the second stand-by period is shorter than the first stand-by period.

19. The threshold estimation apparatus according to claim 1, wherein, before subjecting the living subject to a single unit of a rehabilitation therapy, the threshold estimation apparatus estimates a threshold of the living subject, which estimated threshold is defined as a pre-intervention threshold;

after subjecting the living subject to the single unit of the rehabilitation therapy, the threshold estimation apparatus again estimates a threshold of the living subject, which estimated threshold is defined as a post-intervention threshold; and the threshold estimation apparatus comparatively presents the pre-intervention threshold and the post-intervention threshold.

20. The threshold estimation apparatus according to claim 1, wherein:

the first stand-by period is determined as a shortest interval between two stimuli to a same location of the living subject in which the living subject can recover from a previous stimulus of the two stimuli before a following stimulus of the two stimuli is applied; and the second stand-by period is longer than each time length of stimuli applied to the living subject via the stimulators.

21. The threshold estimation apparatus according to claim 1, wherein the selection:

determines, from the plural stimulators, candidate stimulators that have passed a third stand-by period after the previous stimulation; and selects randomly the stimulator from the determined candidate stimulators.

22. The threshold estimation apparatus according to claim 21, wherein the selection selects randomly the stimulator from the plurality of stimulators when the candidate stimulators cannot be determined.

23. The threshold estimation apparatus according to claim 21, wherein the third stand-by period is between the first and second stand-by periods.

24. The information recording medium according to claim 17, comprising one of a field programmable gate array and an application specific integrated circuit.

* * * * *